United States Patent [19]

Payne et al.

[11] Patent Number: 5,188,960

[45] Date of Patent: Feb. 23, 1993

[54] BACILLUS THURINGIENSIS ISOLATE ACTIVE AGAINST LEPIDOPTERAN PESTS, AND GENES ENCODING NOVEL LEPIDOPTERAN-ACTIVE TOXINS

[75] Inventors: Jewel Payne, San Diego; August J. Sick, Oceanside, both of Calif.

[73] Assignee: Mycogen Corporation, San Diego, Calif.

[21] Appl. No.: 451,261

[22] Filed: Dec. 14, 1989

Related U.S. Application Data

[63] Continuation-in-part of Ser. No. 371,955, Jun. 27, 1989.

[51] Int. Cl.[5] .................. C12N 1/21; C12N 15/32; C12N 15/70; C12N 15/74
[52] U.S. Cl. .................. 435/252.3; 435/69.1; 435/71.2; 435/91; 435/170; 435/172.1; 435/172.3; 435/320.1; 435/832; 530/350; 536/23.71; 935/6; 935/9; 935/22; 935/27; 935/29; 935/59; 935/60; 935/61; 935/64; 935/66; 935/72; 935/73
[58] Field of Search .................. 536/27; 530/350; 435/69.1, 71.2, 170, 91, 172.1, 172.3, 252.31, 320.1, 832, 849; 935/6, 9, 22, 27, 29, 59, 60, 61, 64, 66, 72, 73, 74, 75

[56] References Cited

U.S. PATENT DOCUMENTS 4,448,885  5/1984  Schnepf et al. .................. 435/253
4,467,036  8/1984  Schnepf et al. .................. 435/317

OTHER PUBLICATIONS

Shimizu et al., 1988, Agric. Biol. Chem. 52 (6):1565–1573.
Masson et al., 1989 (Jan.), NAR, 17(1):446.
Schnepf et al., 1985, J Biol. Chem., 260 (10):6264–6272.
Honee et al., 1988, NAR, 16 (13):6240.
Schnepf, H. E. and H. R. Whiteley (1981) "Cloning and Expression of the *Bacillus thuringiensis* crystal protein gene in *Escherichia coli*," Proc. Natl. Acad. Sci. USA vol. 78 5:2893–2897.

*Primary Examiner*—Richard C. Peet
*Attorney, Agent, or Firm*—Saliwanchik & Saliwanchik

[57] ABSTRACT

Novel *Bacillus thuringiensis* genes encoding toxins which are active against lepidopteran insects have been cloned from novel lepidopteran-active *B. thuringiensis* microbes. The DNA encoding the *B. thuringiensis* toxins can be used to transform various prokaryotic and eukaryotic microbes to express the *B. thuringiensis* toxins. These recombinant microbes can be used to control lepidopteran insects in various environments.

13 Claims, 85 Drawing Sheets

A B

```
           10         20         30         40         50         60
  1 ATGGAGATAA TGAATAATCA GAATCAATGC GTTCCTTATA ACTGTTTGAA TGATCCGACA
 61 ATTGAAATAT TAGAAGGAGA AAGAATAGAA ACTGGTTACA CCCCAATAGA TATTTCCTTG
121 TCGCTAACGC AATTTCTGTT GAGTGAATTT GTCCCAGGTG CTGGGTTTGT ATTAGTTTTA
181 ATTGATTTAA TATGGGGGTT TGTGGGTCCC TCTCAATGGG ATGCATTTCT TGTGCAAATT
241 GAACAGTTAA TTAACCAAAG AATAGAGGAA TTCGCTAGGA ACCAAGCAAT TTCTAGATTA 310        320        330        340        350        360
301 GAAGGGCTAA GCAACCTTTA TCAAATTTAC GCAGAAGCTT TTAGAGAGTG GGAAGCAGAT
361 CCTACTAATC CAGCATTAAC AGAAGAGATG CGTATTCAGT TCAATGACAT GAACAGTGCT
421 CTTACACCG CTATTCCTCT TTTTACAGTT CAAAATTATC AAGTACCTCT TCTATCAGTA
481 TATGTTCAAG CTGCAAATTT ACATTATCG ATGTTTCAGT ATGTTCAGT GTTTGGACAA
541 CGTTGGGGAT TGATGTAGC AACAATCAAT AGTCGTTATA ATGATTAAC TAGGCTTATT 610        620        630        640        650        660
601 GGCACCTATA CAGATTATGC TGTACGCTGG TATAATACGG GATTAGAACG TGTATGGGGA
661 CCCGATTCTA GAGATTGGGT AAGGTATAAT CAATTTAGAA GAGAGCTAAC ACTAACTGTA
721 TTAGATATCG TTTCTCTGTT CCCGAACTAT GATAGTAGAA CGTATCCAAT TCGAACAGTT
781 TCCCAATTAA CTAGAGAAAT TTATACAAAC CCAGTATTAG AAAATTTGA TGGTAGTTTT
841 CGTGGAATGG CTCAGAGAAT AGAACAGAAT ATTAGGCAAC CACATCTTAT GGATCCCTT
```

Figure 2A

```
                                                              910         920         930         940         950         960
901   AATAGTATAA  CCATTATATAC  TGATGTGCAT  AGAGGCTTTA  ATTATTGGTC  AGGACATCAA
961   ATAACAGCTT  CTCCTGTCGG   TTTTGCGGGG  CCAGAATTTA  CTTTTCCTAG  ATATGAACC
1021  ATGGAAATG   CTGCTCCACC   CGTACTACTG  TCAACTACTG  GTTTGGGGAT  TTTTAGAACA
1081  TTATCTTCAC  CTCTTTACAG   AAGAATTATA  CTTGGTTCAG  GCCCAAATAA  TCAGAACCTG
1141  TTTGTCCTTG  ATGGAACGGA   ATTTTCTTTT  GCCTCCCTAA  CAGCCGATTT  ACCTTCTACT 1210        1220        1230        1240        1250        1260
1201  ATATACAGAC  AAAGGGGAAC   GGTCGATTCA  CTAGATGTAA  TACCGCCACA  GGATAAATAGT
1261  GTGCCAGCAC  GTGCGGGATT   TAGTCATCGA  TTAAGTCATG  TTACAATGCT  GAGCCAAGCA
1321  GCTGGAGCAG  TTTACACCTT   GAGAGCTCCA  ACGTTTTCTT  GGCGACATCG  TAGTGCTGAA
1381  TTCTCTAACC  TAATTCCTTC   ATCACAAATC  ACACAGATAC  CTTTAACAAA  GTCTATTAAT
1441  CTTGGCTCTG  GGACCCTCGT   TGTTAAAGGA  CAGGATTTA   CAGGAGGAGA  TATTCTTCGA 1510        1520        1530        1540        1550        1560
1501  AGAACTTCAC  CTGGCCAGAT   TTCAACCTTA  AGAGTGACTA  TTACTGCACC  ATTATCACAA
1561  AGATATCGCG  TAAGAATTCG   CTACGCTTCT  ACTACAAATT  TACAATTCCA  TACATCAATT
1621  GACGGAAGAC  CTATTAATCA   GGGAATTTT   TCAGCAACTA  TGAGTAGTGG  GGTAATTTA
1681  CAGTCCGGAA  GCTTTAGGAC   TGCAGGTTTT  ACTACTCCGT  TTAACTTTTC  AAATGGATCA
1741  AGTATATTTA  CGTTAAGTGC   TCATGTCTTC  AATTCAGGCA  ATGAAGTTTA  TATAGATCGA
```

Figure 2B

```
1801 ATTGAATTTG TTCCGGCAGA AGTAACATTT GAGGCGGAAT ATGATTTAGA AAGAGCGCAA
1861 GAGGCGGTGA ATGCTCTGTT TACTTCTTCC AATCAACTAG GATTAAAAAC AAATGTGACG
1921 GACTATCATA TTGATCAAGT GTCCAATCTA GTCGAATGTT TATCCGGTGA ATTCTGTCTG
1981 GATGAAAAGA GAGAATTGTC CGAGAAAGTC AAACATGCGA AGCGACTCAG TGATGAGCGG
2041 AATTTACTTC AAGACCCAAA CTTCAGAGGC ATCAATAGAC AACCAGACCG TGGCTGGAGA

2101 GGCAGTACGG ATATTACCAT CCAAGGAGGA GATGACGTAT TCAAAGAGAA TTACGTCACA
2161 CTACCGGGTA CCTTTAATGA GTGTTATCCT ACGTATCTGT ATCAAAAAT AGATGAGTCG
2221 AAATAAAAG CCTATACCCG TTACCAATTA AGAGGGTACA TCGAGGATAG TCAAGACTTA
2281 GAAATCTATT TAATTCGCTA CAATACAAAA CACGAAAACAG TAAATGTGCC AGGTACGGGT
2341 TCCTTATGGC CGCTTTCAGT CGAAAATCCA ATTGGAAAGT GCGGAGAACC AAATCGATGC

2401 GCACCACAAC TTGAATGGAA TCCTGATCTA GATTGTTCCT GCAGAGACGG GGAAAAATGT
2461 GCACATCACT CCCATCATTT CTCCTTGGAC ATTGATATTG GATGTACAGA TTTAAATGAG
2521 AACTTAGGTG TATGGTGAT ATTCAAAATT AAGACGCAAG ATGGTCACGC AAGACTAGGT
2581 AATCTAGAGT TTCTCGAAGA TTCTCGAAGA GTAGGCAATA CGTTAGCACG CGTGAAGAGA
2641 GCGGAGAAGA AGTGGAGAGA CAAACGAGAG AAATTGCAAG TGGAAACAAA TATCGTTTAT
```

Figure 2C

```
2701 AAAGAGGCAA AAGAATCTGT AGATGCTTTA TTTGTGAACT CTCAATATGA TAGATTACAA
2761 GCGGATACCG ACATCGCGAT GATTCATGCG GCAGATAAAC GCGTTCATCG AATTCGAGAA
2821 GCATATCTTC CAGAGTTATC TGTAATTCCG GGTGTCAATG CGGGCATTTT TGAAGAATTA
2881 GAGGACGTA TTTTCACAGC CTACTCTTTA TATGATGCGA GAAATGTCAT TAAAAATGGC
2941 GATTTCAATA ATGGCTTATC ATGCTGGAAC GTGAAAGGGC ATGTAGATGT AGAAGAACAA

3001 AACAACCACC GTTCGGTTCT TGTTGTCCCG GAATGGGAAG CAGAGGTGTC ACAAGAGGTT
3061 CGTGTCTGTC CAGGTCGTGG CTATATCCTA CGTGTTACAG CGTACAAAGA GGGATATGGA
3121 GAAGGTGCG TAACGATTCA TGAGATCGAA GACAATACAG ACGAACTGAA ATTCAGCAAC
3181 TGTGTAGAAG AGGAAGTATA TCCAAACAAC ACGGTAACGT GTAATGATTA TACTGCAAAT
3241 CAAGAAGAAT ACGGGGTGC GTACACTTCT CGTAATCGTG GATATGGTGA ATCTTATGAA

3301 AGTAATTCTT CCATACCAGC TGAGTATGCG CCAGTTTATG AGGAAGCATA TATAGATGGA
3361 AGAAAAGAGA ATCCTTGTGA ATCTAACAGA GGATATGGGG ATTACACGCC ACTACCAGCT
3421 GGTTATGTGA CAAAGAATT AGAGTACTTC CCAGAAACCG ATAAGGTATG GATTGAGATC
3481 GGGGAAACGG AAGGAACATT CATCGTGGAT AGCGTGGAAT TACTCCTTAT GGAGGAA*

Segment 1-*

```
                 5                  10                 15
  1  Met Glu Ile Met Asn Asn Gln Asn Gln Cys Val Pro Tyr Asn Cys
 16  Leu Asn Asp Pro Thr Ile Glu Leu Ile Glu Gly Glu Arg Ile Glu
 31  Thr Gly Tyr Thr Pro Ile Asp Ser Leu Ser Leu Thr Gln Phe
 46  Leu Leu Ser Glu Val Pro Gly Ala Phe Gly Val Leu Gly Leu
 61  Ile Asp Leu Ile Trp Gly Phe Gly Pro Ser Gln Trp Asp Ala
 76  Phe Leu Val Gln Ile Glu Gln Leu Ile Asn Gln Arg Ile Glu Glu
 91  Phe Ala Arg Asn Gln Ala Ile Ser Arg Leu Glu Gly Leu Ser Asn
106  Leu Tyr Gln Ile Tyr Ala Glu Ala Phe Arg Glu Trp Glu Ala Asp
121  Pro Thr Asn Pro Ala Leu Thr Glu Glu Met Arg Ile Gln Phe Asn
136  Asp Met Asn Ser Ala Leu Thr Thr Ala Ile Pro Leu Phe Thr Val
151  Gln Asn Tyr Gln Val Pro Leu Leu Ser Val Tyr Val Gln Ala Ala
166  Asn Leu His Leu Ser Val Leu Arg Asp Val Ser Val Phe Gly Gln
181  Arg Trp Gly Phe Asp Ala Ala Thr Ile Asn Ser Arg Tyr Asn Asp
196  Leu Thr Arg Leu Ile Gly Asn Tyr Thr Asp Tyr Ala Val Arg Trp
211  Tyr Asn Thr Gly Leu Glu Arg Val Trp Gly Pro Asp Ser Arg Asp
```

```
226 Trp Val Arg Tyr Asn Gln Phe Arg Arg Glu Leu Thr Leu Thr Val
241 Leu Asp Ile Val Ser Leu Phe Pro Asn Tyr Asp Ser Arg Thr Tyr
256 Pro Ile Arg Thr Val Ser Gln Leu Thr Arg Glu Ile Tyr Thr Asn
271 Pro Val Leu Glu Asn Phe Asp Gly Ser Phe Arg Gly Met Ala Gln
286 Arg Ile Glu Asn Ile Arg Gln Pro His Leu Met Asp Leu Leu
301 Asn Ser Ile Thr Tyr Asp Val His Arg Gly Phe Asn Tyr
316 Trp Gly His Gln Ile Ile Thr Ala Ser Pro Val Gly Phe Ala Gly
331 Pro Glu Thr Phe Pro Arg Tyr Gly Thr Met Gly Asn Ala Ala
346 Pro Pro Val Leu Ile Ser Thr Thr Gly Leu Gly Ile Phe Arg Thr
361 Leu Ser Ser Pro Leu Tyr Arg Arg Ile Ile Leu Gly Ser Gly Pro
376 Asn Asn Gln Leu Phe Val Leu Asp Gly Thr Glu Phe Ser Phe
391 Ala Ser Leu Thr Ala Asp Leu Pro Ser Thr Ile Tyr Arg Gln Arg
406 Gly Thr Val Asp Ser Leu Asp Val Ile Pro Pro Gln Asp Asn Ser
421 Val Pro Ala Arg Ala Gly Phe Ser His Arg Leu Ser His Val Thr
436 Met Leu Ser Gln Ala Ala Gly Ala Val Tyr Thr Leu Arg Ala Pro
```

Figure 3B

| | | | | | | | | | | | | | | |
|---|---|---|---|---|---|---|---|---|---|---|---|---|---|---|
| 451 | Thr | Phe | Ser | Trp | Arg | His | Arg | Ser | Ala | Glu | Phe | Ser | Asn | Leu | Ile |
| 466 | Pro | Ser | Ser | Gln | Ile | Thr | Gln | Ile | Val | Pro | Leu | Thr | Lys | Ser | Ile | Asn |
| 481 | Leu | Gly | Ser | Gly | Thr | Ser | Val | Lys | Gly | Pro | Gly | Phe | Thr | Gly | 
| 496 | Gly | Asp | Ile | Leu | Arg | Arg | Thr | Ser | Pro | Gly | Gln | Ile | Ser | Thr | Leu |
| 511 | Arg | Val | Thr | Ile | Thr | Ala | Pro | Leu | Ser | Arg | Tyr | Arg | Val | Arg |
| 526 | Ile | Arg | Tyr | Ala | Ser | Thr | Thr | Asn | Leu | Gln | Phe | His | Thr | Ser | Ile |
| 541 | Asp | Gly | Arg | Pro | Ile | Asn | Gln | Gly | Asn | Phe | Ser | Ala | Thr | Met | Ser |
| 556 | Ser | Gly | Asn | Leu | Gln | Ser | Gly | Ser | Phe | Arg | Thr | Ala | Gly | Phe |
| 571 | Thr | Thr | Pro | Phe | Asn | Phe | Ser | Asn | Gly | Ser | Ser | Ile | Phe | Thr | Leu |
| 586 | Ser | Ala | His | Val | Phe | Asn | Ser | Gly | Asn | Glu | Val | Tyr | Ile | Asp | Arg |
| 601 | Ile | Glu | Phe | Val | Pro | Ala | Glu | Val | Thr | Phe | Glu | Ala | Glu | Tyr | Asp |
| 616 | Leu | Glu | Arg | Ala | Gln | Lys | Ala | Val | Asn | Ala | Leu | Phe | Thr | Ser | Ser |
| 631 | Asn | Gln | Leu | Gly | Leu | Lys | Thr | Asn | Val | Thr | Asp | Tyr | His | Ile | Asp |
| 646 | Gln | Val | Ser | Asn | Leu | Val | Glu | Cys | Leu | Ser | Gly | Glu | Phe | Cys | Leu |
| 661 | Asp | Glu | Lys | Arg | Glu | Leu | Ser | Glu | Lys | Val | Lys | His | Ala | Lys | Arg |

Figure 3C

```
676  Leu Ser Asp Glu Arg Asn Leu Leu Gln Asp Pro Asn Phe Arg Gly
691  Ile Asn Arg Gln Pro Asp Arg Gly Val Arg Gly Ser Thr Asp Ile
706  Thr Ile Gln Gly Gly Asp Asp Val Phe Lys Glu Asn Tyr Val Thr
721  Leu Pro Gly Thr Phe Asn Glu Cys Tyr Pro Thr Tyr Leu Tyr Gln
736  Lys Ile Asp Glu Ser Lys Leu Lys Ala Tyr Thr Arg Tyr Gln Leu
751  Arg Gly Tyr Ile Glu Asp Ser Gln Asp Leu Glu Ile Tyr Leu Ile
766  Arg Tyr Asn Thr Lys His Glu Thr Val Asn Val Pro Gly Thr Gly
781  Ser Leu Trp Pro Leu Ser Val Glu Val Ile Gly Lys Cys Gly
796  Glu Pro Asn Arg Cys Ala Pro Gln Leu Asn Trp Asn Pro Asp Leu
811  Asp Cys Ser Cys Arg Asp Gly Glu Lys Cys Ala His Ser His His
826  His Phe Ser Leu Asp Ile Gly Cys Cys Thr Asp Leu Asn Glu
841  Asn Leu Gly Val Trp Val Ile Phe Lys Ile Thr Gln Asp Gly
856  His Ala Arg Leu Gly Asn Leu Glu Phe Leu Glu Lys Pro Leu
871  Val Gly Glu Ser Leu Ala Arg Val Lys Arg Ala Glu Lys Lys Trp
886  Arg Asp Lys Lys Arg Glu Lys Leu Gln Val Glu Thr Asn Ile Val Tyr
```

Figure 3D

| | | | | | | | | | | | | | | | |
|---|---|---|---|---|---|---|---|---|---|---|---|---|---|---|---|
| 901 | Lys | Glu | Ala | Lys | Glu | Ser | Val | Asp | Ala | Leu | Phe | Val | Asn | Ser | Gln |
| 916 | Tyr | Asp | Arg | Leu | Gln | Ala | Asp | Thr | Asp | Ile | Ala | Met | Ile | His | Ala |
| 931 | Ala | Asp | Lys | Arg | Val | His | Arg | Ile | Arg | Glu | Ala | Tyr | Leu | Pro | Glu |
| 946 | Leu | Ser | Val | Ile | Pro | Gly | Val | Asn | Ala | Gly | Ile | Phe | Glu | Glu | Leu |
| 961 | Glu | Gly | Arg | Ile | Phe | Thr | Ala | Tyr | Ser | Leu | Tyr | Asp | Ala | Arg | Asn |
| 976 | Val | Ile | Lys | Asn | Gly | Asp | Phe | Asn | Asn | Gly | Leu | Ser | Cys | Trp | Asn |
| 991 | Val | Lys | Gly | His | Val | Asp | Val | Glu | Glu | Gln | Asn | Asn | His | Arg | Ser |
| 1006 | Val | Leu | Val | Val | Pro | Glu | Trp | Glu | Ala | Glu | Val | Ser | Gln | Glu | Val |
| 1021 | Arg | Val | Cys | Pro | Gly | Arg | Gly | Tyr | Ile | Leu | Arg | Val | Thr | Ala | Tyr |
| 1036 | Lys | Glu | Gly | Tyr | Gly | Glu | Gly | Cys | Val | Thr | Ile | His | Glu | Ile | Glu |
| 1051 | Asp | Asn | Thr | Asp | Glu | Leu | Lys | Phe | Ser | Asn | Cys | Val | Glu | Glu | Glu |
| 1066 | Val | Tyr | Pro | Asn | Asn | Thr | Val | Thr | Cys | Asn | Asp | Tyr | Thr | Ala | Asn |
| 1081 | Gln | Glu | Glu | Tyr | Gly | Gly | Ala | Tyr | Thr | Ser | Arg | Asn | Arg | Gly | Tyr |
| 1096 | Gly | Glu | Tyr | Ser | Glu | Asn | Ser | Ser | Ile | Pro | Ala | Glu | Tyr | Ala |  |
| 1111 | Pro | Val | Tyr | Glu | Glu | Ala | Tyr | Ile | Asp | Gly | Arg | Lys | Glu | Asn | Pro |
| 1126 | Cys | Glu | Ser | Asn | Arg | Gly | Tyr | Gly | Asp | Tyr | Thr | Pro | Leu | Pro | Ala |
| 1141 | Gly | Tyr | Val | Thr | Lys | Glu | Leu | Glu | Tyr | Phe | Pro | Glu | Thr | Asp | Lys |
| 1156 | Val | Trp | Ile | Glu | Ile | Gly | Glu | Thr | Glu | Gly | Thr | Phe | Ile | Val | Asp |
| 1171 | Ser | Val | Glu | Leu | Leu | Leu | Met | Glu | Glu |  |  |  |  |  |  |

Fragment 1-*

Figure 3E

```
        Met Glu Ile Met Asn Asn Gln Asn Cys Val Pro Tyr Asn Cys Leu Asn Asp Pro Thr
        ATG GAG ATA ATG AAT AAT CAA AAT TGC GTT CCT TAT AAC TGT TTG AAT GAT CCG ACA
                        5                  10                 15                 20

Ile Glu Ile Leu Glu Gly Glu Arg Ile Glu Thr Gly Tyr Thr Pro Ile Asp Ile Ser Leu
        ATT GAA ATA TTA GAA GGA GAA AGA ATA GAA ACT GGT TAC ACC CCA ATA GAT ATT TCC TTG
                       25                  30                 35                 40

Ser Leu Thr Gln Phe Leu Leu Ser Glu Phe Val Pro Gly Ala Gly Phe Val Leu Gly Leu
        TCG CTA ACG CAA TTT CTG TTG AGT GAA TTT GTC CCA GGT GCT GGG TTT GTA TTA GGT TTA
                       45                  50                 55                 60

Ile Asp Leu Ile Trp Gly Phe Val Gly Pro Ser Gln Trp Asp Ala Phe Leu Val Gln Ile
        ATT GAT TTA ATA TGG GGA TTT GTG GGT CCC TCT CAA TGG GAT GCA TTT CTT GTG CAA ATT
                       65                  70                 75                 80

Glu Gln Leu Ile Asn Gln Arg Ile Glu Glu Phe Ala Arg Asn Gln Ala Ile Ser Arg Leu
        GAA CAG TTA ATT AAC CAA AGA ATA GAG GAG TTC GCT AGG AAC CAA GCA ATT TCT AGA TTA
                       85                  90                 95                100
```

Figure 4A

```
                    105              110              115              120
Glu Gly Leu Ser Asn Leu Tyr Gln Ile Tyr Ala Glu Ala Phe Arg Glu Trp Glu Ala Asp
GAA GGG CTA AGC AAC CTT TAT CAA ATT TAC GCA GAA GCT TTT AGA GAG TGG GAA GCA GAT 125              130              135              140
Pro Thr Asn Pro Ala Leu Thr Glu Glu Met Arg Ile Gln Phe Asn Asp Met Asn Ser Ala
CCT ACT AAT CCA GCA TTA ACA GAA GAG ATG CGT ATT CAG TTC AAT GAC ATG AAC AGT GCT 145              150              155              160
Leu Thr Thr Ala Ile Pro Leu Phe Thr Val Gln Asn Tyr Gln Val Pro Leu Leu Ser Val
CTT ACA ACC GCT ATT CCT CTT ACA GTT CAA AAT TAT CAA GTA CCT CTT CTA TCA GTA 165              170              175              180
Tyr Val Gln Ala Ala Asn Leu His Leu Ser Val Leu Arg Asp Val Ser Val Phe Gly Gln
TAT GTT CAA GCT GCA AAT TTA CAT TTA TCG GTT TTG AGA GAT GTT TCA GTG TTT GGA CAA 185              190              195              200
Arg Trp Gly Phe Asp Val Ala Thr Ile Asn Ser Arg Tyr Asn Asp Leu Thr Arg Leu Ile
CGT TGG GGA TTT GAT GTA GCA ACA ATC AAT AGT CGT TAT AAT GAT TTA ACT AGG CTT ATT
```

Figure 4B

|   |   |   | 205 |   |   |   |   | 210 |   |   |   |   | 215 |   |   |   |   | 220 |
|---|---|---|---|---|---|---|---|---|---|---|---|---|---|---|---|---|---|---|
| Gly | Thr | Tyr | Thr | Asp | Tyr | Ala | Val | Arg | Trp | Tyr | Asn | Thr | Gly | Leu | Glu | Arg | Val | Trp | Gly |
| GGC | ACC | TAT | ACA | GAT | TAT | GCT | GTA | CGC | TGG | TAT | AAT | ACG | GGA | TTA | GAA | CGT | GTA | TGG | GGA |

|   |   |   | 225 |   |   |   |   | 230 |   |   |   |   | 235 |   |   |   |   | 240 |
|---|---|---|---|---|---|---|---|---|---|---|---|---|---|---|---|---|---|---|
| Pro | Asp | Ser | Arg | Asp | Trp | Val | Arg | Tyr | Asn | Gln | Phe | Arg | Arg | Glu | Leu | Thr | Leu | Thr | Val |
| CCG | GAT | TCT | AGA | GAT | TGG | GTA | AGG | TAT | AAT | CAA | TTT | AGA | AGA | GAG | CTA | ACA | CTA | ACT | GTA |

|   |   |   | 245 |   |   |   |   | 250 |   |   |   |   | 255 |   |   |   |   | 260 |
|---|---|---|---|---|---|---|---|---|---|---|---|---|---|---|---|---|---|---|
| Leu | Asp | Ile | Val | Ser | Leu | Phe | Pro | Asn | Tyr | Asp | Ser | Arg | Thr | Tyr | Pro | Ile | Arg | Thr | Val |
| TTA | GAT | ATC | GTT | TCT | CTG | TTC | CCG | AAC | TAT | GAT | AGT | AGA | ACG | TAT | CCA | ATT | CGA | ACA | GTT |

|   |   |   | 265 |   |   |   |   | 270 |   |   |   |   | 275 |   |   |   |   | 280 |
|---|---|---|---|---|---|---|---|---|---|---|---|---|---|---|---|---|---|---|
| Ser | Gln | Leu | Thr | Arg | Glu | Ile | Tyr | Thr | Asn | Pro | Val | Leu | Glu | Asn | Phe | Asp | Gly | Ser | Phe |
| TCC | CAA | TTA | ACT | AGA | GAA | ATT | TAT | ACA | AAC | CCA | GTA | TTA | GAA | AAT | TTT | GAT | GGT | AGT | TTT |

|   |   |   | 285 |   |   |   |   | 290 |   |   |   |   | 295 |   |   |   |   | 300 |
|---|---|---|---|---|---|---|---|---|---|---|---|---|---|---|---|---|---|---|
| Arg | Gly | Met | Ala | Gln | Arg | Ile | Glu | Gln | Asn | Ile | Arg | Gln | Pro | His | Leu | Met | Asp | Leu | Leu |
| CGT | GGA | ATG | GCT | CAG | AGA | ATA | GAA | CAG | AAT | ATT | AGG | CAA | CCA | CAT | CTT | ATG | GAT | CTC | CTT |

```
            305              310              315              320
Asn Ser Ile Thr Tyr Thr Asp Val His Arg Gly Phe Asn Tyr Trp Ser Gly His Gln
AAT AGT ATA ACC TAT ACT GAT GTG CAT AGA GGC TTT AAT TAT TGG TCA GGA CAT CAA 325              330              335              340
Ile Thr Ala Ser Pro Val Gly Phe Ala Gly Pro Glu Phe Thr Phe Pro Arg Tyr Gly Thr
ATA ACA GCT TCT CCT GTC GGT TTT GCG GGG CCA GAA TTT ACT TTT CCT AGA TAT GGA ACC 345              350              355              360
Met Gly Asn Ala Ala Pro Pro Val Leu Ile Ser Thr Thr Gly Ile Phe Arg Thr
ATG GGA AAT GCT CCA CCC GTA CTG ATC TCA ACT ACT GGT ATT TTT AGA ACA 365              370              375              380
Leu Ser Ser Pro Leu Tyr Arg Arg Ile Leu Gly Ser Gly Pro Asn Asn Gln Asn Leu
TTA TCT TCA CCT CTT TAC AGA AGA ATT CTT GGT TCA GGC CCA AAT CAG AAC CTG 385              390              395              400
Phe Val Leu Asp Gly Thr Glu Phe Ser Phe Ala Ser Leu Thr Ala Asp Leu Pro Ser Thr
TTT GTC CTT GAT GGA ACG GAA TTT TCT GCC TCC CTA ACA GCC GAT TTA CCT TCT ACT
```

Figure 4E

```
                    405                     410                     415                     420
Ile Tyr Arg Gln Arg Gly Thr Val Asp Ser Leu Asp Val Ile Pro Gln Asp Asn Ser
ATA TAC AGA CAA AGG GGA ACG GTC GAT TCA CTA GAT GTA ATA CCG CAG GAT AAT AGT 425                     430                     435                     440
Val Pro Ala Arg Ala Gly Phe Ser His Val Arg Leu Ser His Val Thr Met Leu Ser Gln Ala
GTG CCA GCA CGT GCG GGA TTT AGT CAT GTT CGA TTA AGT CAT GTT ACA ATG CTG AGC CAA GCA 445                     450                     455                     460
Ala Gly Ala Val Tyr Thr Leu Arg Ala Pro Thr Phe Ser Trp Arg His Arg Ser Ala Glu
GCT GGA GCA GTT TAC ACC TTG AGA GCT CCA ACG TTT TCT TGG CGA CAT CGT AGT GCT GAA 465                     470                     475                     480
Phe Ser Asn Leu Ile Pro Ser Ser Gln Ile Thr Gln Ile Pro Leu Thr Lys Ser Ile Asn
TTC TCT AAC CTA ATT CCT TCA TCA CAA ATC ACA CAG ATA CCT TTA ACA AAG TCT ATT AAT 485                     490                     495                     500
Leu Gly Ser Gly Thr Ser Val Val Lys Gly Pro Gly Phe Thr Gly Asp Ile Leu Arg
CTT GGC TCT GGG ACC TCT GTT GTT AAA GGA CCA GGA TTT ACA GGA GAT ATT CTT CGA
```

```
                    505                 510                 515                 520
Arg Thr Ser Pro Gly Gln Ile Ser Thr Leu Arg Val Thr Ile Thr Ala Pro Leu Ser Gln
AGA ACT TCA CCT GGC CAG ATT TCA ACC TTA AGA GTG ACT ATT ACT GCA CCA TTA TCA CAA 525                 530                 535                 540
Arg Tyr Arg Val Arg Ile Arg Tyr Ala Ser Thr Thr Asn Leu Gln Phe His Thr Ser Ile
AGA TAT CGC GTA AGA ATT CGC TAC GCT TCT ACT ACA AAT TTA CAA TTC CAT ACA TCA ATT 545                 550                 555                 560
Asp Gly Arg Pro Ile Asn Gln Gly Asn Phe Ser Ala Thr Met Ser Ser Gly Gly Asn Leu
GAC GGA AGA CCT ATT AAT CAG GGG AAT TTT TCA GCA ACT ATG AGT AGT GGG GGT AAT TTA 565                 570                 575                 580
Gln Ser Gly Ser Phe Arg Thr Ala Gly Phe Thr Thr Pro Phe Asn Phe Ser Asn Gly Ser
CAG TCC GGA AGC TTT AGG ACT GCA GGT TTT ACT CCG TTT AAC TTT TCA AAT GGA TCA 585                 590                 595                 600
Ser Ile Phe Thr Leu Ser Ala His Val Phe Asn Ser Gly Asn Glu Val Tyr Ile Asp Arg
AGT ATA TTT ACG TTA AGT GCT CAT GTC TTC AAT TCA GGC AAT GAA GTT TAT ATA GAT CGA
```

Figure 4F

|     |     |     | 605 |     |     |     |     | 610 |     |     |     |     | 615 |     |     |     |     | 620 |     |
| --- | --- | --- | --- | --- | --- | --- | --- | --- | --- | --- | --- | --- | --- | --- | --- | --- | --- | --- | --- |
| Ile | Glu | Phe | Val | Pro | Ala | Glu | Val | Thr | Phe | Glu | Ala | Tyr | Asp | Leu | Glu | Arg | Ala | Gln |
| ATT | GAA | TTT | GTT | CCG | GCA | GAA | GTA | ACA | TTT | GAG | GCG | TAT | GAT | TTA | GAA | AGA | GCG | CAA |

|     |     |     | 625 |     |     |     |     | 630 |     |     |     |     | 635 |     |     |     |     | 640 |     |
| --- | --- | --- | --- | --- | --- | --- | --- | --- | --- | --- | --- | --- | --- | --- | --- | --- | --- | --- | --- |
| Glu | Ala | Val | Asn | Ala | Leu | Phe | Thr | Ser | Asn | Gln | Leu | Gly | Leu | Lys | Thr | Asn | Val | Thr |
| GAG | GCG | GTG | AAT | GCT | CTG | TTT | ACT | TCC | AAT | CAA | CTA | GGA | TTA | AAA | ACA | AAT | GTG | ACG |

|     |     |     | 645 |     |     |     |     | 650 |     |     |     |     | 655 |     |     |     |     | 660 |     |
| --- | --- | --- | --- | --- | --- | --- | --- | --- | --- | --- | --- | --- | --- | --- | --- | --- | --- | --- | --- |
| Asp | Tyr | His | Ile | Asp | Gln | Val | Ser | Asn | Leu | Val | Glu | Cys | Leu | Ser | Gly | Glu | Phe | Cys | Leu |
| GAC | TAT | CAT | ATT | GAT | CAA | GTG | TCC | AAT | CTA | GTC | GAA | TGT | TTA | TCC | GGT | GAA | TTC | TGT | CTG |

|     |     |     | 665 |     |     |     |     | 670 |     |     |     |     | 675 |     |     |     |     | 680 |     |
| --- | --- | --- | --- | --- | --- | --- | --- | --- | --- | --- | --- | --- | --- | --- | --- | --- | --- | --- | --- |
| Asp | Glu | Lys | Arg | Glu | Leu | Ser | Glu | Lys | Val | Lys | His | Ala | Lys | Arg | Leu | Ser | Asp | Glu | Arg |
| GAT | GAA | AAG | AGA | GAA | TTG | TCC | GAG | AAA | GTC | AAA | CAT | GCG | AAG | CGA | CTC | AGT | GAT | GAG | CGG |

|     |     |     | 685 |     |     |     |     | 690 |     |     |     |     | 695 |     |     |     |     | 700 |     |
| --- | --- | --- | --- | --- | --- | --- | --- | --- | --- | --- | --- | --- | --- | --- | --- | --- | --- | --- | --- |
| Asn | Leu | Gln | Asp | Pro | Asn | Phe | Arg | Gly | Ile | Asn | Arg | Gln | Pro | Asp | Arg | Gly | Trp | Arg |
| AAT | TTA | CTT | CAA | GAC | AAC | TTC | AGA | GGC | ATC | AAT | AGA | CAA | CCA | GAC | CGT | GGC | TGG | AGA |

Figure 4G

```
Gly Ser Thr Asp Ile Thr Gln Gly Asp Val Phe Lys Glu Asn Tyr Val Thr
GGC AGT ACG GAT ATT ACC CAA GGA GAT GTA TTC AAA GAG AAT TAC GTC ACA
        705             710             715             720

Leu Pro Gly Thr Phe Asn Glu Cys Tyr Pro Thr Tyr Leu Tyr Gln Lys Ile Asp Glu Ser
CTA CCG GGT ACC TTT AAT GAG TGT TAT CCT ACG TAT CTG TAT CAA AAA ATA GAT GAG TCG
        725             730             735             740

Lys Leu Lys Ala Tyr Thr Arg Tyr Gln Leu Arg Tyr Ile Glu Asp Ser Gln Asp Leu
AAA TTA AAA GCC TAT ACC CGT TAC CAA TTA AGA GGG TAC ATC GAG GAT AGT CAA GAC TTA
        745             750             755             760

Glu Ile Tyr Leu Ile Arg Tyr Asn Thr Lys His Glu Thr Val Asn Val Pro Gly Thr Gly
GAA ATC TAT TTA ATT CGC TAC AAT ACA AAA CAC GAA ACA GTA AAT GTG CCA GGT ACG GGT
        765             770             775             780

Ser Leu Trp Pro Leu Ser Val Glu Asn Pro Ile Gly Lys Cys Gly Glu Pro Asn Arg Cys
TCC TTA TGG CCG CTT TCA GTC GAA AAT CCA ATT GGA AAG TGC GGA GAA CCA AAT CGA TGC
        785             790             795             800
```

Figure 4H

```
                          805              810              815              820
Ala Pro Gln Leu Glu Trp Asn Pro Asp Leu Asp Cys Ser Cys Arg Asp Gly Glu Lys Cys
GCA CCA CAA CTT GAA TGG AAT CCT GAT CTA GAT TGT TCC TGC AGA GAC GGG GAA AAA TGT 825              830              835              840
Ala His His Ser His Phe Ser Leu Asp Ile Asp Ile Gly Cys Thr Asp Leu Asn Glu
GCA CAT CAC TCC CAT TTC TCC TTG GAC ATT GAT ATT GGA TGT ACA GAT TTA AAT GAG 845              850              855              860
Asn Leu Gly Val Trp Val Ile Phe Lys Thr Gln Asp Gly His Ala Arg Leu Gly
AAC TTA GGT GTA TGG GTG ATA TTC AAA ACG CAA GAT GGT CAC GCA AGA CTA GGT 865              870              875              880
Asn Leu Glu Phe Leu Glu Glu Lys Pro Val Gly Glu Ser Leu Ala Arg Val Lys Arg
AAT CTA GAG TTT CTC GAA GAG AAA CCA GTA GGC GAA TCG TTA GCA CGC GTG AAG AGA 885              890              895              900
Ala Glu Lys Lys Trp Arg Asp Lys Arg Glu Lys Leu Gln Val Glu Thr Asn Ile Val Tyr
GCG GAG AAG AAG TGG AGA GAC AAA CGA GAG AAA TTG CAA GTG GAA ACA AAT ATC GTT TAT
```

Figure 4I

```
                905                910             915               920
Lys Glu Ala Lys Glu Ser Val Asp Ala Leu Phe Val Asn Ser Gln Tyr Asp Arg Leu Gln
AAA GAG GCA AAA GAA TCT GTA GAT GCT TTA TTT GTG AAC TCT CAA TAT GAT AGA TTA CAA 925             930               935               940
Ala Asp Thr Asp Ile Ala Met Ile His Ala Ala Asp Lys Arg Val His Arg Ile Arg Glu
GCG GAT ACC GAC ATC GCG ATG ATT CAT GCG GCA GAT AAA CGC GTT CAT CGA ATT CGA GAA 945             950               955               960
Ala Tyr Leu Pro Glu Leu Ser Val Ile Pro Gly Val Asn Ala Gly Ile Phe Glu Glu Leu
GCA TAT CTT CCA GAG TTA TCT GTA ATT CCG GGT GTC AAT GCG GGC ATT TTT GAA GAA TTA 965             970               975               980
Glu Gly Arg Ile Phe Thr Ala Tyr Ser Leu Tyr Asp Ala Arg Asn Val Ile Lys Asn Gly
GAG GGA CGT ATT TTC ACA GCC TAC TCT TTA TAT GAT GCG AGA AAT GTC ATT AAA AAT GGC 985             990               995              1000
Asp Phe Asn Asn Gly Leu Ser Cys Trp Asn Val Lys Gly His Val Asp Val Glu Glu Gln
GAT TTC AAT AAT GGC TTA TCA TGC TGG AAC GTG AAA GGG CAT GTA GAT GTA GAA GAA CAA
```

Figure 4J

```
           1005                              1015              1020
Asn Asn His Arg Ser Val Leu Val Val Pro Glu Trp Glu Ala Glu Val Ser Gln Glu Val
AAC AAC CAC CGT TCG GTT CTT GTT GTC CCG GAA TGG GAA GCA GAG GTG TCA CAA GAG GTT 1025                              1035              1040
Arg Val Cys Pro Gly Arg Gly Tyr Ile Leu Arg Val Thr Ala Tyr Lys Glu Gly Tyr Gly
CGT GTC TGT CCA GGT CGT GGC TAT ATC CTA CGT GTT ACA GCG TAC AAA GAG GGA TAT GGA 1045                              1055              1060
Glu Gly Cys Val Thr Ile His Glu Ile Glu Asp Asn Thr Asp Leu Lys Phe Ser Asn
GAA GGT TGC GTA ACG ATT CAT GAG ATC GAG GAC AAT ACA GAC CTG AAA TTC AGC AAC 1065                              1075              1080
Cys Val Glu Glu Val Tyr Pro Asn Asn Thr Val Thr Cys Asn Asp Tyr Thr Ala Asn
TGT GTA GAG GAG GTA TAT CCA AAC AAC ACG GTA ACG TGT AAT GAT TAT ACT GCA AAT 1085                              1095              1100
Gln Glu Tyr Gly Gly Ala Tyr Thr Ser Arg Asn Arg Gly Tyr Gly Gln Ser Tyr Glu
CAA GAA TAC GGG GGT GCG TAC ACT TCT CGT AAT CGT GGA TAT GGT GAA TCT TAT GAA
```

Figure 4K

```
                         1105              1110              1115              1120
Ser Asn Ser Ser Ile Pro Ala Glu Tyr Ala Pro Val Tyr Glu Ala Tyr Ile Asp Gly
AGT AAT TCT TCT ATA CCA GCT GAG TAT GCG CCA GTT TAT GAG GAA GCA TAT ATA GAT GGA 1125              1130              1135              1140
Arg Lys Glu Asn Pro Cys Glu Ser Asn Arg Gly Tyr Gly Asp Tyr Thr Pro Leu Pro Ala
AGA AAA GAG AAT CCT TGT GAA TCT AAC AGA GGA TAT GGG GAT TAC ACG CCA CTA CCA GCT 1145              1150              1155              1160
Gly Tyr Val Thr Lys Glu Leu Glu Tyr Phe Pro Glu Thr Asp Lys Val Trp Ile Glu Ile
GGT TAT GTG ACA AAA GAA TTA GAG TAC TTC CCA GAA ACC GAT AAG GTA TGG ATT GAG ATC 1165              1170              1175
Gly Glu Thr Glu Gly Thr Phe Ile Val Asp Ser Val Glu Leu Leu Leu Met Glu Glu
GGG GAA ACG GAA GGA ACA TTC ATC GTG GAT AGC GTG GAA TTA CTC CTT ATG GAG GAA
```

Figure 4L

```
        10         20         30         40         50         60
  1 ATGGAAATAA ATAATCAAAA CCAATGTGTG CCTTACAATT GTTTAAGTAA TCCTAAGGAG
 61 ATATATTAG GCGAGGAAAG GCTAGAAACA GGGAATACTG TAGCAGACAT TTCATTAGGG
121 CTTATTAATT TTCTATATTC TAATTTGTA CCAGGAGGAG GATTTATAGT AGGTTTACTA
181 GAATTAATAT GGGATTTAT AGGGCCTTCG CAATGGGATA TTTTTTTAGC TCAAATTGAG
241 CAATTGATTA GTCAAAGAAT AGAAGAATTT GCTAGGAATC AGGCAATTTC AAGATTGGAG
        310        320        330        340        350        360
301 GGGCTAAGCA ATCTTTATAA GGTCTATGTT AGAGCGTTTA GCGACTGGGA GAAAGATCCT
361 ACTAATCCTG CTTAAGGGA AGAAATGCGT ATACAATTTA ATGACATGAA TAGTGCTCTC
421 ATAACGGCTA TCCCACTTTT TAGAGTTCAA AATTATGAAG TTGCTCTTTT ATCTGTATAT
481 GTTCAAGCCG CAAACTTACA TTTATCTATT TTAAGGGATG TTTCAGTTTT CGGAGAAAGA
541 TGGGGATATG ATACAGCGAC TATCAATAAT CGCTATAGTG ATCTGACTAG CCTTATTCAT
        610        620        630        640        650        660
601 GTTTATACTA ACCATTGTGT GGATACGTAT AATCAGGGAT TAAGGCGTTT GGAAGGTCGT
661 TTTCTTAGCG ATTGGATTGT ATATAATCGT TTCCGGAGAC AATTGACAAT TTCAGTATTA
721 GATATTGTTG CGTTTTTCC AAATTATGAT ATTAGAACAT ATCCAATTCA AACAGCTACT
781 CAGCTAACGA GGGAAGTCTA TCTGGATTTA CCTTTTATTA ATGAAAATCT TTCTCCTGCA
841 GCAAGCTATC CAACCTTTTC AGCTGCTGAA AGTGCTATAA TTAGAAGTCC TCATTTAGTA
```

Figure 5A

```
            910        920        930        940        950        960
 901 GACTTTTTAA ATAGCTTTAC CATTTATACA GATAGTCTGG CACGTTATGC ATATTGGGGA
 961 GGGCACTTGG TAAATTCTTT CCGCACAGGA ACCACTACTA ATTTGATAAG ATCCCCTTTA
1021 TATGGAAGGG AAGGAAATAC AGAGCGCCCC GTAACTATTA CCGCATCACC TAGCGTACCA
1081 ATATTTAGAA CACTTTCATA TATTACAGGC CTTGACAATT CAAATCCTGT AGCTGGAATC
1141 GAGGGAGTGG AATTCCAAAA TACTATAAGT AGAAGTATCT ATCGTAAAAG CGGTCCAATA 1210       1220       1230       1240       1250       1260
1201 GATTCTTTTA GTGAATTACC ACCTCAAGAT GCCAGCGTAT CTCCTGCAAT TGGGTATAGT
1261 CACCGTTTAT GCCATGCAAC ATTTTTAGAA CGGATTAGTG GACCAAGAAT AGCAGGCACC
1321 GTATTTCTT GGACACACCG TAGTGCCAGC CCTACTAATG AAGTAAGTCC ATCTAGAATT
1381 ACACAAATTC CATGGGTAAA GGCGCATACT CTTGCATCTG GTGCCTCCGT CATTAAAGGT
1441 CCTGGATTTA CAGGTGGAGA TATTCTGACT AGGAATAGTA TGGGCGAGCT GGGGACCTTA 1510       1520       1530       1540       1550       1560
1501 CGAGTAACCT TCACAGGAAG ATTACCACAA AGTTATTATA TACGTTTCCG TTATGCTTCG
1561 GTAGCAAATA GGAGTGGTAC ATTTAGATAT TCACAGCCAC CTTCGTATGG AATTTCATTT
1621 CCAAAAACTA TGGACGCAGG TGAACCACTA ACATCTCGTT CGTTCGCTCA TACAACACTC
1681 TTCACTCCAA TAACCTTTTC ACGAGCTCAA GAAGAATTTG ATCTATACAT CCAATCGGGT
1741 GTTTATATAG ATCGAATTGA ATTTATACCG GTTACTGCAA CATTTGAGGC AGAATATGAT
```

Figure 5B

```
              1810       1820       1830       1840       1850       1860
1801    TTAGAAAGAG CGCAAAAGGT GGTGAATGCC CTGTTTACGT CTACAAACCA ACTAGGGCTA
1861    AAAACAGATG TGACGGATTA TCATATTGAT CAGGTATCCA ATCTAGTTGC GTGTTTATCG
1921    GATGAATTTT GTCTGGATGA AAAGAGAGAA TTGTCCGAGA AAGTAAACA  TGCAAAGCGA
1981    CTCAGTGATG AGCGGAATTT ACTTCAAGAT CCAAACTTCA GAGGGATCAA TAGGCAACCA
2041    GACCGTGGCT GGAGAGGAAG TACGGATATT ACTATCCAAG GAGGAGATGA CGTATTCAAA 2110       2120       2130       2140       2150       2160
2101    GAGAATTACG TTACGCTACC GGGTACCTTT GATGAGTGCT ATCCAACGTA TTTATATCAA
2161    AAAATAGATG AGTCGAAATT AAAAGCCTAT ACCCGTTATC AATTAAGAGG GTATATCGAA
2221    GATAGTCAAG ACTTAGAAAT CTATTTAATT CGTTACAATG CAAAACACGA AATAGTAAAT
2281    GTACCAGGTA CAGGAAGTTT ATGGCCTCTT TCTGTAGAAA ATCAAATTGG ACCTTGTGGA
2341    GAACCGAATC GATGCGCGCC ACACCTTGAA TGGAATCCTG ATTACACTG  TTCCTGCAGA 2410       2420       2430       2440       2450       2460
2401    GACGGGGAAA AATGTGCACA TCATTCTCAT CATTTCTCTT TGGACATTGA TGTTGGATGT
2461    ACAGACTTAA ATGAGGACTT AGGTGTATGG AGATTAAGAC GCAAGATGGC
2521    CACGCACGAC TAGGAATCT  AGAGTTCTC  GAAGAGAAC  CATTATTAGG AGAAGCACTA
2581    GCTCGTGTGA AAAGAGCGGA GAAAAATGG  AGAGACAAAC GCGAAACATT ACAATGGAA
2641    ACAACTATCG TTTATAAAGA GGCAAAAGAA TCTGTAGATG CTTTATTTGT AAACTCTCAA
```

Figure 5C

```
2701 TATGATAGAT TACAAGCGGA TACGAACATC GCGATGATTC ATGCGGCAGA TAAACGCGTT
2761 CATAGAATTC GAGAAGCGTA TCTGCCGGAG CTGTCTGTGA TTCCGGGTGT CAATGCGGCT
2821 ATTTTGAAG  AATTAGAAGA GCGTATTTTC ACTGCATTTT CCCTATATGA TGCGAGAAAT
2881 ATTATTAAAA ATGGCGATTT CAATAATGGC TTATTATGCT GGAACGTGAA AGGGCATGTA
2941 GAGGTAGAAG AACAAAAACA TCACCGTTCA GTCCTGGTTA TCCCAGAATG GGAGGCAGAA 2710       2720       2730       2740       2750       2760

3001 GTGTCACAAG AGGTTCGTGT CTGTCCAGGT CGTGGCTATA TCCTTCGTGT TACAGCGTAC
3061 AAAGAGGGAT ATGGAGAAGG ATCCATGAGA TCGAGAACAA TACAGACGAA
3121 CTGAAATTCA ACAACTGTGT GTATATCCAA ACAACACGGT AACGTGTATT
3181 AATTATACTG CGACTCAAGA AGAAATATGAG GGTACGTACA CTTCTCGTAA TCGAGGATAT
3241 GACGAAGCCT ATGGTAATAA CCCTTCCGTA CCAGCTGATT ATGCGTCAGT CTATGAAGAA 3010       3020       3030       3040       3050       3060

3301 AAATCGTATA CAGATAGACG AAGAGAGAAT CCTTGTGAAT CTAACAGAGG ATATGGAGAT
3361 TACACCAC   TACCAGCTGG TTATGTAACA AAGGAATTAG AGTACTTCCC AGAGACCGAT
3421 AAGGTATGGA TTGAGATTGG AGAAACAGAA GGAACATTCA TCGTGGACAG CGTGGAATTA
3481 CTCCCTTATGG AGGAA*

Segment 140-3634

|   |     |     |     |     |     | 5   |     |     |     |     | 10  |     |     |     |     | 15  |
|---|-----|-----|-----|-----|-----|-----|-----|-----|-----|-----|-----|-----|-----|-----|-----|-----|
| 1   | Met | Glu | Ile | Asn | Asn | Gln | Asn | Cys | Val | Pro | Tyr | Asn | Cys | Leu |
| 16  | Ser | Asn | Pro | Lys | Glu | Ile | Leu | Gly | Glu | Glu | Arg | Leu | Glu | Thr |
| 31  | Gly | Asn | Thr | Val | Ala | Asp | Ile | Ser | Leu | Gly | Leu | Ile | Asn | Phe | Leu |
| 46  | Tyr | Ser | Asn | Phe | Val | Pro | Gly | Gly | Phe | Ile | Val | Gly | Leu | Leu |
| 61  | Glu | Leu | Ile | Trp | Gly | Phe | Ile | Gly | Pro | Ser | Gln | Trp | Asp | Ile | Phe |
| 76  | Leu | Ala | Gln | Ile | Glu | Gln | Leu | Ile | Ser | Gln | Arg | Ile | Glu | Glu | Phe |
| 91  | Ala | Arg | Asn | Gln | Ala | Ile | Ser | Arg | Leu | Glu | Gly | Leu | Ser | Asn | Leu |
| 106 | Tyr | Lys | Val | Tyr | Val | Arg | Ala | Phe | Ser | Asp | Trp | Glu | Lys | Asp | Pro |
| 121 | Thr | Asn | Pro | Ala | Leu | Arg | Glu | Glu | Met | Arg | Ile | Gln | Phe | Asn | Asp |
| 136 | Met | Asn | Ser | Ala | Leu | Ile | Thr | Ala | Ile | Pro | Leu | Phe | Arg | Val | Gln |
| 151 | Asn | Tyr | Glu | Val | Ala | Leu | Leu | Ser | Val | Tyr | Val | Gln | Ala | Ala | Asn |
| 166 | Leu | His | Leu | Ser | Ile | Leu | Arg | Asp | Val | Ser | Val | Phe | Gly | Glu | Arg |
| 181 | Trp | Gly | Tyr | Asp | Thr | Ala | Thr | Ile | Asn | Asn | Arg | Tyr | Ser | Asp | Leu |
| 196 | Thr | Ser | Leu | Ile | His | Val | Tyr | Thr | Asn | His | Cys | Val | Asp | Thr | Tyr |
| 211 | Asn | Gln | Gly | Leu | Arg | Arg | Leu | Glu | Gly | Arg | Phe | Leu | Ser | Asp | Trp |

Figure 6A

```
226 Ile Val Tyr Asn Arg Phe Arg Gln Leu Thr Ile Ser Val Leu
241 Asp Ile Val Ala Phe Phe Asn Tyr Asp Ile Arg Thr Tyr Pro
256 Ile Gln Thr Ala Thr Gln Leu Arg Glu Val Tyr Leu Asp Leu
271 Pro Phe Ile Asn Glu Asn Ser Pro Ala Ala Ser Tyr Pro Thr
286 Phe Ser Ala Ala Glu Ser Ala Ile Ile Arg Ser Pro His Leu Val
301 Asp Phe Leu Asn Ser Phe Thr Tyr Thr Asp Ser Leu Ala Arg
316 Tyr Ala Tyr Trp Gly Gly His Val Asn Ser Phe Arg Thr Gly
331 Thr Thr Asn Leu Ile Arg Ser Pro Leu Tyr Gly Arg Glu Gly
346 Asn Thr Glu Arg Pro Val Thr Ile Thr Ala Ser Pro Ser Val Pro
361 Ile Phe Arg Thr Leu Ser Tyr Ile Thr Gly Leu Asp Asn Ser Asn
376 Pro Val Ala Gly Ile Glu Gly Val Glu Phe Gln Asn Thr Ile Ser
391 Arg Ser Ile Tyr Arg Lys Ser Gly Pro Ile Asp Ser Phe Ser Glu
406 Leu Pro Pro Gln Asp Ala Ser Val Ser Pro Ala Ile Gly Tyr Ser
421 His Arg Leu Cys His Ala Thr Phe Leu Glu Arg Ile Ser Gly Pro
436 Arg Ile Ala Gly Thr Val Phe Ser Trp Thr His Arg Ser Ala Ser
```

Figure 6B

```
451 Pro Thr Asn Glu Val Ser Pro Ser Arg Ile Thr Gln Ile Pro Trp
466 Val Lys Ala His Thr Leu Ala Ser Gly Ala Ser Val Ile Lys Gly
481 Pro Gly Phe Thr Gly Gly Asp Ile Leu Thr Arg Asn Ser Met Gly
496 Glu Leu Gly Thr Leu Arg Val Thr Phe Thr Gly Arg Leu Pro Gln
511 Ser Tyr Tyr Ile Arg Phe Arg Tyr Ala Ser Val Ala Asn Arg Ser
526 Gly Thr Phe Arg Tyr Ser Gln Pro Pro Ser Tyr Gly Ile Ser Phe
541 Pro Lys Thr Met Asp Ala Gly Glu Pro Leu Thr Ser Arg Ser Phe
556 Ala His Thr Thr Leu Phe Thr Pro Ile Thr Phe Ser Arg Ala Gln
571 Glu Glu Phe Asp Leu Tyr Ile Gln Ser Gly Val Tyr Ile Asp Arg
586 Ile Glu Phe Ile Pro Val Thr Ala Thr Phe Glu Ala Glu Tyr Asp
601 Leu Glu Arg Ala Gln Lys Val Val Asn Ala Leu Phe Thr Ser Thr
616 Asn Gln Leu Gly Leu Lys Thr Asp Val Thr Asp Tyr His Ile Asp
631 Gln Val Ser Asn Leu Val Ala Cys Leu Ser Asp Glu Phe Cys Leu
646 Asp Glu Lys Arg Glu Leu Ser Glu Lys Val Lys His Ala Lys Arg
661 Leu Ser Asp Glu Arg Asn Leu Leu Gln Asp Pro Asn Phe Arg Gly
```

Figure 6C

```
676  Ile Asn Arg Gln Pro Asp Arg Gly Trp Arg Gly Ser Thr Asp Ile
691  Thr Ile Gln Gly Gly Asp Val Phe Lys Glu Asn Tyr Val Thr
706  Leu Pro Gly Thr Phe Asp Glu Cys Tyr Pro Thr Tyr Leu Tyr Gln
721  Lys Ile Asp Phe Ser Lys Leu Ala Tyr Leu Arg Tyr Gln Leu
736  Arg Gly Tyr Ile Glu Asp Ser Gln Asp Leu Glu Ile Tyr Leu Ile
751  Arg Tyr Asn Ala Lys His Glu Ile Val Asn Val Pro Gly Thr Gly
766  Ser Leu Trp Pro Leu Ser Val Glu Asn Gln Ile Gly Pro Cys Gly
781  Glu Pro Asn Arg Cys Ala Pro His Leu Glu Trp Asn Pro Asp Leu
796  His Cys Ser Cys Arg Asp Gly Lys Cys Ala His Ser His Ser His
811  His Phe Ser Leu Asp Ile Asp Val Gly Cys Thr Asp Leu Asn Glu
826  Asp Leu Gly Val Trp Val Ile Phe Lys Ile Lys Thr Gln Asp Gly
841  His Ala Arg Leu Gly Asn Leu Glu Phe Leu Glu Lys Pro Leu
856  Leu Gly Glu Ala Leu Ala Arg Val Lys Arg Ala Glu Lys Lys Trp
871  Arg Asp Lys Arg Glu Gln Thr Leu Gln Leu Glu Thr Thr Ile Val Tyr
886  Lys Glu Ala Lys Glu Ser Val Asp Ala Leu Phe Val Asn Ser Gln
```

Figure 6D

```
 901 Tyr Asp Arg Leu Gln Ala Asp Thr Asn Ile Ala Met Ile His Ala
 916 Ala Asp Lys Arg Val His Arg Ile Arg Glu Ala Tyr Leu Pro Glu
 931 Leu Ser Val Ile Pro Gly Val Asn Ala Ala Ile Phe Glu Glu Leu
 946 Glu Arg Arg Phe Thr Ala Phe Ser Leu Tyr Asp Ala Arg Asn
 961 Ile Ile Lys Asn Gly Asp Phe Asn Gly Leu Leu Cys Trp Asn
 976 Val Lys Gly His Val Glu Val Gln Asn Asn His Arg Ser
 991 Val Leu Val Ile Pro Glu Trp Glu Ala Glu Val Ser Gln Glu Val
1006 Arg Val Cys Pro Gly Arg Gly Tyr Ile Leu Arg Val Thr Ala Tyr
1021 Lys Glu Gly Tyr Gly Glu Gly Cys Val Thr Ile His Glu Ile Glu
1036 Asn Asn Thr Asp Glu Leu Lys Phe Asn Cys Val Glu Glu Glu Glu
1051 Val Tyr Pro Asn Asn Thr Val Thr Cys Ile Asn Tyr Thr Ala Thr
1066 Gln Glu Glu Tyr Glu Gly Thr Tyr Thr Ser Arg Asn Arg Gly Tyr
1081 Asp Glu Ala Tyr Gly Asn Asn Pro Ser Val Pro Ala Asp Tyr Ala
1096 Ser Val Tyr Glu Glu Lys Ser Tyr Thr Asp Arg Arg Arg Glu Asn
1111 Pro Cys Glu Ser Asn Arg Gly Tyr Gly Asp Tyr Thr Pro Leu Pro
1126 Ala Gly Tyr Val Thr Lys Glu Leu Glu Tyr Phe Pro Glu Thr Asp
1141 Lys Val Trp Ile Glu Ile Gly Glu Thr Glu Gly Thr Phe Ile Val
1156 Asp Ser Val Glu Leu Leu Leu Met Glu Glu
```

Fragment 1-*

```
    1               5                10               15               20
Met Glu Ile Asn Asn Gln Asn Cys Val Pro Tyr Asn Cys Leu Ser Asn Pro Lys Glu
ATG GAA ATA AAT AAT CAA AAC TGT GTG CCT TAC AAT TGT TTA AGT AAT CCT AAG GAG 25               30               35               40
Ile Ile Leu Gly Glu Arg Leu Glu Thr Gly Asn Thr Val Ala Asp Ile Ser Leu Gly
ATA ATA TTA GGC GAG AGG CTA GAA ACA GGG AAT ACA GTA GCA GAC ATT TCA TTA GGG 45               50               55               60
Leu Ile Asn Phe Leu Tyr Ser Asn Phe Val Pro Gly Gly Phe Ile Val Gly Leu Leu
CTT ATT AAT TTT CTA TAT TCT AAT TTT GTA CCA GGA GGA TTT ATA GTA GGT TTA CTA 65               70               75               80
Glu Leu Ile Trp Gly Phe Ile Gly Pro Ser Gln Trp Asp Ile Phe Leu Ala Gln Ile Glu
GAA TTA ATA TGG GGA TTT ATA GGG CCT TCG CAA TGG GAT ATT TTT TTA GCT CAA ATT GAG 85               90               95              100
Gln Leu Ile Ser Gln Arg Ile Glu Phe Ala Arg Asn Gln Ala Ile Ser Arg Leu Glu
CAA TTG ATT AGT CAA AGA ATA GAA TTT GCT AGG AAT CAG GCA ATT TCA AGA TTG GAG
```

|     |     |     |     |     | 105 |     |     |     | 110 |     |     |     | 115 |     |     |     | 120 |
| --- | --- | --- | --- | --- | --- | --- | --- | --- | --- | --- | --- | --- | --- | --- | --- | --- | --- |
| Gly | Leu | Ser | Asn | Tyr | Leu | Lys | Val | Tyr | Val | Arg | Ala | Phe | Ser | Asp | Trp | Glu | Lys | Asp | Pro |
| GGG | CTA | AGC | AAT | TAT | CTT | AAG | GTC | TAT | GTT | AGA | GCG | TTT | AGC | GAC | TGG | GAG | AAA | GAT | CCT |

|     |     |     |     | 125 |     |     |     |     | 130 |     |     |     |     | 135 |     |     |     |     | 140 |
| --- | --- | --- | --- | --- | --- | --- | --- | --- | --- | --- | --- | --- | --- | --- | --- | --- | --- | --- | --- |
| Thr | Asn | Pro | Ala | Leu | Arg | Glu | Glu | Met | Arg | Ile | Gln | Phe | Asn | Asp | Met | Asn | Ser | Ala | Leu |
| ACT | AAT | CCT | GCT | CTA | AGG | GAA | GAA | ATG | CGT | ATA | CAA | TTT | AAT | GAC | ATG | AAT | AGT | GCT | CTC |

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Ile | Thr | Ala | Ile | Pro | Leu | Phe | Arg | Val | Gln | Asn | Tyr | Glu | Val | Ala | Leu | Leu | Ser | Val | Tyr |
| ATA | ACG | GCT | ATT | CCA | CTT | TTT | AGA | GTT | CAA | AAT | TAT | GAA | GTT | GCT | CTT | TTA | TCT | GTA | TAT |

|     |     |     |     | 165 |     |     |     |     | 170 |     |     |     |     | 175 |     |     |     |     | 180 |
| --- | --- | --- | --- | --- | --- | --- | --- | --- | --- | --- | --- | --- | --- | --- | --- | --- | --- | --- | --- |
| Val | Gln | Ala | Ala | Asn | Leu | His | Leu | Ser | Ile | Leu | Arg | Asp | Val | Ser | Val | Phe | Gly | Glu | Arg |
| GTT | CAA | GCC | GCA | AAC | TTA | CAT | TTA | TCT | ATT | TTA | AGG | GAT | GTT | TCA | GTT | TTC | GGA | GAA | AGA |

|     |     |     |     | 185 |     |     |     |     | 190 |     |     |     |     | 195 |     |     |     |     | 200 |
| --- | --- | --- | --- | --- | --- | --- | --- | --- | --- | --- | --- | --- | --- | --- | --- | --- | --- | --- | --- |
| Trp | Gly | Tyr | Asp | Thr | Ala | Thr | Ile | Asn | Asn | Arg | Tyr | Ser | Asp | Leu | Thr | Ser | Leu | Ile | His |
| TGG | GGA | TAT | GAT | ACA | GCG | ACT | ATC | AAT | AAT | CGC | TAT | AGT | GAT | CTG | ACT | AGC | CTT | ATT | CAT |

Figure 7B

```
                   205                   210                   215                   220
Val Tyr Thr Asn His Cys Val Asp Thr Asn Gln Gly Leu Arg Arg Leu Glu Gly Arg
GTT TAT ACT AAC CAT TGT GTG GAT ACG AAT CAG GGA TTA AGG CGT TTG GAA GGT CGT 225                   230                   235                   240
Phe Ser Asp Trp Ile Val Tyr Asn Arg Phe Arg Gln Leu Thr Ile Ser Val Leu
TTT CTT AGC TGG ATT GTA TAT AAT CGT TTC CGG AGA CAA TTG ACA ATT TCA GTA TTA 245                   250                   255                   260
Asp Ile Val Ala Phe Phe Pro Asn Tyr Asp Ile Arg Thr Tyr Pro Ile Gln Thr Ala Thr
GAT ATT GTT GCG TTT TTT CCA AAT TAT GAT ATT AGA ACA TAT CCA ATT CAA ACA GCT ACT 265                   270                   275                   280
Gln Leu Thr Arg Glu Val Tyr Leu Asp Leu Pro Phe Ile Asn Glu Asn Leu Ser Pro Ala
CAG CTA ACG AGG GAA GTC TAT CTG GAT TTA CCT TTT ATT AAT GAA AAT CTT TCT CCT GCA 285                   290                   295                   300
Ala Ser Tyr Pro Thr Phe Ser Ala Ala Glu Ser Ala Ile Ile Ile Arg Ser Pro His Leu Val
GCA AGC TAT CCA ACC TTT TCA GCT GCT GAA AGT GCT ATA ATT AGA AGT CCT CAT TTA GTA
```

Figure 7C

```
                 305             310             315             320
Asp Phe Leu Asn Ser Phe Thr Ile Tyr Thr Asp Ser Leu Ala Arg Tyr Ala Tyr Trp Gly
GAC TTT TTA AAT AGC TTT ACC ATT TAT ACA GAT AGT CTG GCA CGT TAT GCA TAT TGG GGA 325             330             335             340
Gly His Leu Val Asn Ser Phe Arg Thr Thr Gly Thr Thr Asn Leu Ile Arg Ser Pro Leu
GGG CAC TTG GTA AAT TCT TTC CGC ACA GGA ACC ACT AAT TTG ATA AGA TCC CCT TTA 345             350             355             360
Tyr Gly Arg Glu Gly Asn Thr Glu Arg Pro Val Thr Ile Thr Ala Ser Pro Ser Val Pro
TAT GGA AGG GAA GGA AAT ACA GAG CGC CCC GTA ACT ATT ACC GCA TCA CCT AGC GTA CCA 365             370             375             380
Ile Phe Arg Thr Leu Ser Tyr Ile Thr Gly Leu Asp Asn Ser Asn Pro Val Ala Gly Ile
ATA TTT AGA ACA CTT TCA TAT ATT ACA GGC CTT GAC AAT TCA AAT CCT GTA GCT GGA ATC 385             390             395             400
Glu Gly Val Glu Phe Gln Asn Thr Ile Ser Arg Ile Tyr Arg Lys Ser Gly Pro Ile
GAG GGA GTG GAA TTC CAA AAT ACT ATA AGT AGA ATT TAT CGT AAA AGC GGT CCA ATA
```

```
                           405                         410                         415                         420
Asp Ser   Phe Glu   Leu Pro   Pro Gln   Asp Ala   Ser Val   Ser Pro   Ala Ile   Gly Tyr   Ser
GAT TCT   TTT GAA   TTA CCA   CCT CAA   GAT GCC   AGC GTA   TCT CCT   GCA ATT   GGG TAT   AGT 425                         430                         435                         440
His Arg   Leu Cys   His Ala   Thr Phe   Leu Glu   Arg Ile   Ser Gly   Pro Arg   Ile Ala   Gly Thr
CAC CGT   TTA TGC   CAT GCA   ACA TTT   TTA GAA   CGG ATT   AGT GGA   CCA AGA   ATA GCA   GGC ACC 445                         450                         455                         460
Val Phe   Ser Trp   Thr His   Arg Ser   Ala Ser   Pro Thr   Asn Glu   Val Ser   Pro Ser   Arg Ile
GTA TTT   TCT TGG   ACA CAC   CGT AGT   GCC AGC   CCT ACT   AAT GAA   GTA AGT   CCA TCT   AGA ATT 465                         470                         475                         480
Thr Gln   Ile Pro   Val Lys   Ala His   Thr Leu   Ala Ser   Gly Ala   Ser Val   Ile Lys   Gly
ACA CAA   ATT CCA   GTA AAG   GCG CAT   ACT CTT   GCA TCT   GGT GCC   TCC GTC   ATT AAA   GGT 485                         490                         495                         500
Pro Gly   Phe Thr   Gly Gly   Asp Ile   Leu Thr   Arg Asn   Ser Met   Gly Glu   Leu Gly   Thr Leu
CCT GGA   TTT ACA   GGT GGA   GAT ATT   CTG ACT   AGG AAT   AGT ATG   GGC GAG   CTG GGG   ACC TTA
```

|     |     |     | 505 |     |     |     |     | 510 |     |     |     |     | 515 |     |     |     |     | 520 |
| --- | --- | --- | --- | --- | --- | --- | --- | --- | --- | --- | --- | --- | --- | --- | --- | --- | --- | --- |
| Arg | Val | Thr | Phe | Gly | Arg | Leu | Pro | Gln | Ser | Tyr | Tyr | Ile | Arg | Phe | Arg | Tyr | Ala | Ser |
| CGA | GTA | ACC | TTC | GGA | AGA | TTA | CCA | CAA | AGT | TAT | TAT | ATA | CGT | TTC | CGT | TAT | GCT | TCG |

|     |     |     | 525 |     |     |     |     | 530 |     |     |     |     | 535 |     |     |     |     | 540 |
| --- | --- | --- | --- | --- | --- | --- | --- | --- | --- | --- | --- | --- | --- | --- | --- | --- | --- | --- |
| Val | Ala | Asn | Arg | Ser | Gly | Thr | Phe | Arg | Tyr | Ser | Gln | Pro | Pro | Tyr | Gly | Ile | Ser | Phe |
| GTA | GCA | AAT | AGG | AGT | GGT | ACA | TTT | AGA | TAT | TCA | CAG | CCA | CCT | TAT | GGA | ATT | TCA | TTT |

|     |     |     | 545 |     |     |     |     | 550 |     |     |     |     | 555 |     |     |     |     | 560 |
| --- | --- | --- | --- | --- | --- | --- | --- | --- | --- | --- | --- | --- | --- | --- | --- | --- | --- | --- |
| Pro | Lys | Thr | Met | Asp | Ala | Gly | Glu | Pro | Leu | Thr | Ser | Arg | Ser | Phe | Ala | His | Thr | Thr | Leu |
| CCA | AAA | ACT | ATG | GAC | GCA | GGT | GAA | CCA | CTA | ACA | TCT | CGT | TCG | TTC | GCT | CAT | ACA | ACA | CTC |

|     |     |     | 565 |     |     |     |     | 570 |     |     |     |     | 575 |     |     |     |     | 580 |
| --- | --- | --- | --- | --- | --- | --- | --- | --- | --- | --- | --- | --- | --- | --- | --- | --- | --- | --- |
| Phe | Thr | Pro | Ile | Thr | Phe | Ser | Arg | Ala | Gln | Glu | Glu | Phe | Asp | Leu | Tyr | Ile | Gln | Ser | Gly |
| TTC | ACT | CCA | ATA | ACC | TTT | TCA | CGA | GCT | CAA | GAA | GAA | TTT | GAT | CTA | TAC | ATC | CAA | TCG | GGT |

|     |     |     | 585 |     |     |     |     | 590 |     |     |     |     | 595 |     |     |     |     | 600 |
| --- | --- | --- | --- | --- | --- | --- | --- | --- | --- | --- | --- | --- | --- | --- | --- | --- | --- | --- |
| Val | Tyr | Ile | Asp | Arg | Ile | Phe | Glu | Pro | Val | Thr | Ala | Thr | Phe | Glu | Ala | Glu | Tyr | Asp |
| GTT | TAT | ATA | GAT | CGA | ATT | TTT | GAA | CCG | GTT | ACT | GCA | ACA | TTT | GAG | GCA | GAA | TAT | GAT |

```
                            605                       610                       615                       620
Leu Glu Arg Ala Gln Lys Val Val Asn Ala Leu Phe Thr Ser Asn Gln Leu Gly Leu
TTA GAA AGA GCG CAA AAG GTG GTG AAT GCC CTG TTT ACG TCT AAC CAA CTA GGG CTA 625                       630                       635                       640
Lys Thr Asp Val Thr Asp Tyr His Ile Asp Gln Val Ser Asn Leu Val Ala Cys Leu Ser
AAA ACA GAT GTG ACG GAT TAT CAT ATT GAT CAG GTA TCC AAT CTA GTT GCG TGT TTA TCG 645                       650                       655                       660
Asp Glu Phe Cys Leu Asp Glu Lys Arg Glu Leu Ser Glu Lys Val Lys His Ala Lys Arg
GAT GAA TTT TGT CTG GAT GAA AAG AGA GAA TTG TCC GAG AAA GTT AAA CAT GCA AAG CGA 665                       670                       675                       680
Leu Ser Asp Glu Arg Asn Leu Leu Gln Asp Pro Asn Phe Arg Gly Ile Asn Arg Gln Pro
CTC AGT GAT GAG CGG AAT TTA CTT CAA GAT CCA AAC TTC AGA GGG ATC AAT AGG CAA CCA 685                       690                       695                       700
Asp Arg Gly Trp Arg Gly Ser Thr Asp Ile Thr Ile Gln Gly Asp Asp Val Phe Lys
GAC CGT GGC TGG AGA GGA AGT ACG GAT ATT ACT ATC CAA GGA GAT GAC GTA TTC AAA
```

|     |     | 705 |     |     | 710 |     |     | 715 |     |     | 720 |
| --- | --- | --- | --- | --- | --- | --- | --- | --- | --- | --- | --- |
| Glu | Asn Tyr Val | Thr | Leu Pro Gly | Thr | Phe Asp Glu | Cys | Tyr Pro Thr | Tyr | Leu Tyr Gln |
| GAG | AAT TAC GTT | ACG | CTA CCG GGT | ACC | TTT GAT GAG | TGC | TAT CCA ACG | TAT | TTA TAT CAA |

|     |     | 725 |     |     | 730 |     |     | 735 |     |     | 740 |
| --- | --- | --- | --- | --- | --- | --- | --- | --- | --- | --- | --- |
| Lys | Ile Asp Glu | Ser | Lys Leu Lys | Ala | Tyr Thr Arg | Tyr | Gln Leu Arg | Gly | Tyr Ile Glu |
| AAA | ATA GAT GAG | TCG | AAA TTA AAA | GCC | TAT ACC CGT | TAT | CAA TTA AGA | GGG | TAT ATC GAA |

|     |     | 745 |     |     | 750 |     |     | 755 |     |     | 760 |
| --- | --- | --- | --- | --- | --- | --- | --- | --- | --- | --- | --- |
| Asp | Ser Gln Asp | Leu | Glu Ile Tyr | Leu | Arg Tyr Asn | Ala | Lys His Glu | Ile | Val Asn |
| GAT | AGT CAA GAC | TTA | GAA ATC TAT | TTA | CGT TAC AAT | GCA | AAA CAC GAA | ATA | GTA AAT |

|     |     | 765 |     |     | 770 |     |     | 775 |     |     | 780 |
| --- | --- | --- | --- | --- | --- | --- | --- | --- | --- | --- | --- |
| Val | Pro Gly Thr | Gly | Ser Leu Trp | Pro | Leu Ser Val | Glu | Asn Gln Ile | Gly | Pro Cys Gly |
| GTA | CCA GGT ACA | GGA | AGT TTA TGG | CCT | CTT TCT GTA | GAA | AAT CAA ATT | GGA | CCT TGT GGA |

|     |     | 785 |     |     | 790 |     |     | 795 |     |     | 800 |
| --- | --- | --- | --- | --- | --- | --- | --- | --- | --- | --- | --- |
| Glu | Pro Asn Arg | Cys | Ala Pro His | Leu | Glu Trp Asn | Pro | Asp Leu His | Cys | Ser Cys Arg |
| GAA | CCG AAT CGA | TGC | GCG CCA CAC | CTT | GAA TGG AAT | CCT | GAT TTA CAC | TGT | TCC TGC AGA |

Figure 7H

```
                    805                     810                     815                     820
Asp Gly Lys Glu Ala His His Ser Leu Phe Ser Cys Ile Asp Val Gly Cys
GAC GGG AAA GAA GCA CAT CAT TCT TTG TTC TCT TGT ATT GAT GTT GGA TGT 825                     830                     835                     840
Thr Asp Leu Asn Glu Asp Leu Gly Val Trp Val Ile Phe Lys Thr Gln Asp Gly
ACA GAC TTA AAT GAG GAC TTA GGT GTA TGG GTG ATA TTC AAG ACG CAA GAT GGC 845                     850                     855                     860
His Ala Arg Leu Gly Asn Leu Glu Phe Leu Glu Lys Pro Leu Gly Glu Ala Leu
CAC GCA CGA CTA GGG AAT CTA GAG TTT CTC GAA AAA CCA TTA GGA GAA GCA CTA 865                     870                     875                     880
Ala Arg Val Lys Ala Glu Lys Lys Trp Arg Asp Lys Arg Thr Leu Gln Leu Glu
GCT CGT GTG AAA GCG GAG AAA AAA TGG AGA GAC AAA CGC ACA TTA CAA TTG GAA 885                     890                     895                     900
Thr Thr Ile Val Tyr Lys Glu Ala Lys Glu Ser Val Asp Ala Leu Phe Val Asn Ser Gln
ACA ACT ATC GTT TAT AAA GAG GCA AAA GAA TCT GTA GAT GCT TTA TTT GTA AAC TCT CAA
```

Figure 7I

```
            905             910             915             920
Tyr Asp Arg Leu Gln Ala Asp Thr Asn Ile Ala Met Ile His Ala Asp Lys Arg Val
TAT GAT AGA TTA CAA GCG GAT ACG AAC ATC GCG ATG ATT CAT GCA GAT AAA CGC GTT 925             930             935             940
His Arg Ile Arg Glu Ala Tyr Leu Pro Glu Leu Ser Val Ile Pro Gly Val Asn Ala Ala
CAT AGA ATT CGA GAA GCG TAT CTG CCG GAG CTG TCT GTG ATT CCG GGT GTC AAT GCG GCT 945             950             955             960
Ile Phe Glu Glu Leu Glu Glu Arg Ile Phe Thr Ala Phe Ser Leu Tyr Asp Ala Arg Asn
ATT TTT GAA GAA TTA GAA GAG CGT ATT TTC ACT GCA TTT TCC CTA TAT GAT GCG AGA AAT 965             970             975             980
Ile Lys Asn Gly Asp Phe Asn Asn Gly Leu Leu Cys Trp Asn Val Lys Gly His Val
ATT AAA AAT GGC GAT TTC AAT AAT GGC TTA TTA TGC TGG AAC GTG AAA GGG CAT GTA 985             990             995             1000
Glu Val Glu Gln Asn Asn His Arg Ser Val Leu Val Ile Pro Glu Trp Glu Ala Glu
GAG GTA GAA CAA AAC AAT CAC CGT TCA GTC CTG GTT ATC CCA GAA TGG GAG GCA GAA
```

Figure 7J

```
                   1005                1010                1015                1020
Val Ser Gln Glu Val Arg Val Cys Pro Gly Arg Gly Tyr Ile Leu Arg Val Thr Ala Tyr
GTG TCA CAA GAG GTT CGT GTC TGT CCA GGT CGT GGC TAT ATC CTT CGT GTT ACA GCG TAC 1025                1030                1035                1040
Lys Glu Gly Tyr Gly Cys Val Thr Ile His Glu Ile Asn Asn Thr Asp Glu
AAA GAG GGA TAT GGA TGC GTA ACG ATC CAT GAG ATC AAT AAC ACA GAC GAA 1045                1050                1055                1060
Leu Lys Phe Asn Asn Cys Val Glu Glu Val Tyr Pro Asn Thr Val Thr Cys Ile
CTG AAA TTC AAC AAC TGT GTA GAA GAG GTA TAT CCA AAC ACG GTA ACG TGT ATT 1065                1070                1075                1080
Asn Tyr Thr Ala Thr Gln Glu Tyr Glu Gly Thr Tyr Thr Ser Arg Asn Arg Gly Tyr
AAT TAT ACT GCG ACT CAA GAA TAT GAG GGT ACG TAC ACT TCT CGT AAT CGA GGA TAT 1085                1090                1095                1100
Asp Glu Ala Tyr Gly Asn Pro Ser Val Pro Ala Asp Tyr Ser Val Ala Ser Val Tyr Glu Glu
GAC GAA GCC TAT GGT AAT AAC CCT TCC GTA CCA GCT GAT TAT GCG TCA GTC TAT GAA GAA
```

Figure 7K

```
                      1105                    1110                   1115                    1120
Lys Ser Tyr Thr Asp Arg Arg Arg Glu Asn Pro Cys Glu Ser Asn Arg Gly Tyr Gly Asp
AAA TCG TAT ACA GAT AGA AGA CGA GAG AAT CCT TGT GAA TCT AAC AGA GGA TAT GGA GAT
                      1125                    1130                   1135                    1140
Tyr Thr Pro Leu Pro Ala Gly Tyr Val Thr Lys Glu Leu Glu Tyr Phe Pro Glu Thr Asp
TAC ACA CCA CTA CCA GCT GGT TAT GTA ACA AAG GAA TTA GAG TAC TTC CCA GAG ACC GAT
                      1145                    1150                   1155                    1160
Lys Val Trp Ile Glu Ile Gly Glu Thr Glu Gly Thr Phe Ile Val Asp Ser Val Glu Leu
AAG GTA TGG ATT GAG ATT GGA GAA ACA GAA GGA ACA TTC ATC GTG GAC AGC GTG GAA TTA
                      1165
Leu Leu Met Glu Glu
CTC CTT ATG GAG GAA
```

Figure 7L

```
              10         20         30         40         50         60
  1   ATGGAGGAAA ATAATCAAAA TCAATGCATA CCTTACAATT GTTTAAGTAA TCCTGAAGAA
 61   GTACTTTTGG ATGGAGAACG GATATCAACT GGTAATTCAT CAATTGATAT TTCTCTGTCA
121   CTTGTTCAGT TTCTTCGTAT TAACTTTGTA CCAGGGGGAG GATTTTTAGT TGGATTAATA
181   GATTTTGTAT GGGAATAGT  TGGCCCCTCT CATTTCTAGT ACAAATTGAA
241   CAATTAATTA ATGAAAGAAT AGCTGAATTT GCTAGGAATG CTGCTATTGC TAATTTAGAA
              310        320        330        340        350        360
301   GGATTAGGAA ACAATTTCAA TATATATGTG GAAGCATTTA AAGAATGGGA AGAAGATCCT
361   AATAATCCAG CAACCAGGAC CAGAGTAATT GATCGCTTTC GTATACTTGA TGGGCTACTT
421   GAAAGGGACA TCCTTCGTT  TCGAATTTCT GGATTTGAAG TACCCCTTTT ATCCGTTTAT
481   GCTCAAGCGG CCAATCTGCA TCTAGCTATA TTAAGAGATT CTGTAATTTT TGGAGAAAGA
541   TGGGGATTGA CAACGATAAA TGTCAATGAA AACTATAATA GACTAATTAG GCATATTGAT
              610        620        630        640        650        660
601   GAATATATGCTG ATCACTGTGC AAATACGTAT AATCGGGGAT TAAATAATTT ACCGAAATCT
661   ACGTATCAAG ATTGGATAAC ATATAATCGA TTACGGAGAG ACTTAACATT GACTGTATTA
721   GATATCGCCG CTTTCTTTCC AAACTATGAC AATAGGAGAT ATCCAATTCA GCCAGTTGGT
781   CAACTAACAA GGGAAGTTTA TACGGACCCA TTAATTAATT TTAATCCACA GTTACAGTCT
841   GTAGCTCAAT TACCTACTTT TAACGTTATG GAGAGCAGCG CAATTAGAAA TCCTCATTTA

Figure 8A
```

```
              910        920        930        940        950        960
 901   TTTGATATAT TGAATAATCT TACAATCTTT ACGGATTGGT TTAGTGTTGG ACGCAATTTT
 961   TATTGGGGAG GACATCGAGT AATATCTAGC CTTATAGGAG GTGGTAACAT AACATCTCCT
1021   ATATATGGAA GAGAGGCGAA CCAGGAGCCT CCAAGATCCT TTACTTTTAA TGGACCGGTA
1081   TTTAGGACTT TATCAAATCC TACTTTACGA TTATTACAGC AACCTTGGCC AGCGCCACCA
1141   TTTAATTTAC GTGGTGTTGA AGGAGTAGAA TTTTCTACAC CTACAAATAG CTTTACGTAT 1210       1220       1230       1240       1250       1260
1201   CGAGGAAGAG GTACGGTTGA TTCTTTAACT GAATTACCGC CTGAGGATAA TAGTGTGCCA
1261   CCTCGCGAAG GATATAGTCA TCGTTTATGT CATGCAACTT TTGTTCAAAG ATCTGGAACA
1321   CCTTTTTAA  CAACTGGTGT AGTATTTCT  TGGACGCATC GTAGTGCAAC TCTTACAAAT
1381   ACAATTGATC CAGAGAGAAT TAATCAAATA CCTTTAGTGA AAGGATTTAG AGTTTGGGGG
1441   GGCACCCTCTG TCATTACAGG ACCAGGATTT ACAGGAGGGG ATATCCCTCG AAGAAATACC 1510       1520       1530       1540       1550       1560
1501   TTTGGTGATT TTGTATCTCT ACAAGTCAAT ATTAATTCAC CAATTACCCA AAGATACCGT
1561   TTAAGATTTC GTTACGCTTC CAGTAGGGAT GCACGAGTTA TAGTATTAAC AGGAGCGGCA
1621   TCCACAGGAG TGGAGGCCA  AGTTAGTGTA AATATGCCTC TTCAGAAAAC TATGGAAATA
1681   GGGGAGAACT TAACATTAG  AACATTTAGA TATACCGATT TTAGTAATCC TTTTTCATTT
1741   AGAGCTAATC CAGATATAAT TGGGATAAGT GAACAACCTC TATTTGGTGC AGTTCTATT

Figure 8B
```

```
1801 AGTAGCGGTG AACTTTATAT AGATAAAATT GAAATTATTC TAGCAGATGC AACATTTGAA
1861 GCAGAATCTG ATTTAGAAAG AGCACAAAAG GCGGTGAATG CCCTGTTTAC TTCTTCCAAT
1921 CAAATCGGGT TAAAAACCGA TGTGACGGAT TATCATATTG ATCAAGTATC CAATTTAGTG
1981 GATTGTTTAT CAGATGAATT TTGTCTGGAT GAAAAGCGAG AATTGTCCGA GAAAGTCAAA
2041 CATGCGAAGC GACTCAGTGA TGAGCGGAAT TTACTTCAAG ATCCAAACTT CAGAGGGATC

2101 AATAGACAAC CAGACCGTGG CTGGAGAGGA AGTACAGATA TTACCATCCA AGGAGGAGAT
2161 GACGTATTCA AAGAGAATTA CGTCACACTA CCGGGTACCG TTGATGAGTG CTATCCAACG
2221 TATTTATATC AGAAAATAGA TGAGTCGAAA TTAAAAGCTT ATACCCGTTA TGAATTAAGA
2281 GGGTATATCG AAGATAGTCA AGACTTAGAA ATCTATTTGA TCCGTTACAA TGCAAAACAC
2341 GAAATAGTAA ATGTGCCAGG CACGGGTTCC TTTCAGCCCA AAGTCCAATC

2401 GGAAAGTGTG GAGAACCGAA TCGATGCGCG CCACACCTTG AATGGAATCC TGATCTAGAT
2461 TGTTCCTGCA GAGACGGGGA AAAATGTGCA CATCATTCCC ATCATTCAC CTTGGATATT
2521 GATGTTGGAT GTACAGACTT AAATGAGGAC TTAGGTGTAT GGGTGATATT CAAGATTAAG
2581 ACGCAAGATG GCCATGCAAG CTAGGGAAT CTAGAGTTTC TCGAAGAGAA ACCATTATTA
2641 GGGGAAGCAC TAGCTCGTGT GAAAAGAGCG GAGAAGAAGT GGAGAGACAA ACGAGAGAAA
```

Figure 8C

```
      2710        2720        2730        2740        2750        2760
2701  CTGCAGTTGG  AAACAAATAT  TGTTTATAAA  GAGGCAAAAG  AATCTGTAGA  TGCTTTATTT
2761  GTAAACTCTC  AATATGATAG  ATTACAAGTG  GATACGAACA  TCGCAATGAT  TCAATGCGGCA
2821  GATAAACGCG  TTCATAGAAT  CCGGGAAGCG  TATCTGCCAG  AGTTGTCTGT  GATTCCAGGT
2881  GTCAATGCGG  CCATTTTCGA  AGAATTAGAG  GGACGTATTT  TTACAGCGTA  TTCCTTATAT
2941  GATGCGAGAA  ATGTCATTAA  AAATGGCGAT  TTCAATAATG  GCTTATTATG  CTGAACGTG 3010        3020        3030        3040        3050        3060
3001  AAAGGTCATG  TAGATGTAGA  AGAGCAAAAC  AACCACCGTT  CGGTCCTTGT  TATCCCAGAA
3061  TGGGAGGCAG  AAGTGTCACA  AGAGGTTCGT  GTCTGTCCAG  GTCGTGGCTA  TATCCTTCGT
3121  GTCACAGCAT  ATAAAGAGGG  ATATGGAGAG  GGCTGCGTAA  CGATCCATGA  GATCGAAGAC
3181  AATACAGACG  AACTGAAATT  CAGCAACTGT  GTAGAAGAGG  AAGTATATCC  AAACAACACA
3241  GTAACGTGTA  ATAATTATAC  TGGGACTCAA  GAAGAATATG  AGGGTACGTA  CACTTCTCGT 3310        3320        3330        3340        3350        3360
3301  AATCAAGGAT  ATGACGAAGC  CTATGGTAAT  AACCCTTCCG  TACCAGCTGA  TTACGCTTCA
3361  GTCTATGAAG  AAAAATCGTA  TACAGATGGA  CGAAGAGAGA  ATCCTTGTGA  ATCTAACAGA
3421  GGCTATGGGG  ATTACACACC  ACTACCGGCT  GGTTATGTAA  CAAAGGATTT  AGAGTACTTC
3481  CCAGAGACCG  ATAAGGTATG  GATTGAGATC  GGAGAAACAG  AAGGAACATT  CATCGTGGAT
3541  AGCGTGGAAT  TACTCCTTAT  GGAGGAA
```

Segment 1-*

Figure 8D

|     | 1   | 2   | 3   | 4   | 5   | 6   | 7   | 8   | 9   | 10  | 11  | 12  | 13  | 14  | 15  |
| --- | --- | --- | --- | --- | --- | --- | --- | --- | --- | --- | --- | --- | --- | --- | --- |
| 1   | Met | Glu | Asn | Asn | Gln | Asn | Gln | Cys | Ile | Pro | Tyr | Asn | Cys | Leu |     |
| 16  | Ser | Asn | Pro | Glu | Glu | Val | Leu | Leu | Asp | Gly | Glu | Arg | Ile | Ser | Thr |
| 31  | Gly | Asn | Ser | Ser | Ile | Asp | Ile | Ser | Leu | Ser | Leu | Val | Gln | Phe | Leu |
| 46  | Val | Ser | Asn | Phe | Val | Pro | Gly | Gly | Phe | Leu | Val | Gly | Leu | Ile |     |
| 61  | Asp | Phe | Val | Trp | Gly | Ile | Val | Gly | Pro | Ser | Gln | Trp | Asp | Ala | Phe |
| 76  | Leu | Val | Gln | Ile | Glu | Gln | Leu | Ile | Asn | Glu | Arg | Ile | Ala | Glu | Phe |
| 91  | Ala | Arg | Asn | Ala | Ala | Ile | Ala | Asn | Leu | Glu | Gly | Leu | Gly | Asn | Asn |
| 106 | Phe | Asn | Ile | Tyr | Val | Glu | Ala | Phe | Lys | Glu | Trp | Glu | Glu | Asp | Pro |
| 121 | Asn | Asn | Pro | Ala | Thr | Arg | Thr | Arg | Val | Ile | Asp | Arg | Phe | Arg | Ile |
| 136 | Leu | Asp | Gly | Leu | Leu | Glu | Arg | Asp | Ile | Pro | Ser | Phe | Arg | Ile | Ser |
| 151 | Gly | Phe | Glu | Val | Pro | Leu | Leu | Ser | Val | Tyr | Ala | Gln | Ala | Ala | Asn |
| 166 | Leu | His | Leu | Ala | Ile | Leu | Arg | Asp | Ser | Val | Ile | Phe | Gly | Glu | Arg |
| 181 | Trp | Gly | Leu | Thr | Thr | Ile | Asn | Val | Asn | Glu | Asn | Tyr | Asn | Arg | Leu |
| 196 | Ile | Arg | His | Ile | Asp | Glu | Tyr | Ala | Asp | His | Cys | Ala | Asn | Thr | Tyr |
| 211 | Asn | Arg | Gly | Leu | Asn | Asn | Leu | Pro | Lys | Ser | Thr | Tyr | Gln | Asp | Trp |

Figure 9A

```
226  Ile Thr Tyr Asn Arg Leu Arg Arg Asp Leu Thr Leu Thr Val Leu
241  Asp Ile Ala Ala Phe Pro Asn Tyr Asp Asn Arg Arg Tyr Pro
256  Ile Gln Pro Val Gly Gln Leu Thr Arg Glu Val Tyr Thr Asp Pro
271  Leu Ile Asn Phe Asn Pro Gln Leu Ser Gly Val Ala Gln Leu Pro
286  Thr Phe Asn Val Met Glu Ser Ser Ala Ile Arg Asn Pro His Leu
301  Phe Asp Ile Leu Asn Asn Leu Thr Ile Phe Thr Asp Trp Phe Ser
316  Val Gly Arg Asn Phe Tyr Trp Gly Gly His Arg Val Ile Ser Ser
331  Leu Ile Gly Gly Asn Ile Ser Pro Ile Tyr Gly Arg Glu
346  Ala Asn Gln Glu Pro Pro Arg Ser Phe Thr Phe Asn Gly Pro Val
361  Phe Arg Thr Leu Ser Asn Pro Thr Leu Arg Leu Leu Gln Gln Pro
376  Trp Pro Ala Pro Pro Phe Asn Leu Arg Gly Val Glu Gly Val Glu
391  Phe Ser Thr Pro Thr Asn Ser Phe Thr Tyr Arg Gly Arg Gly Thr
406  Val Asp Ser Leu Thr Glu Leu Pro Pro Glu Asp Asn Ser Val Pro
421  Pro Arg Glu Gly Tyr Ser His Arg Leu Cys His Ala Thr Phe Val
436  Gln Arg Ser Gly Gly Thr Pro Phe Leu Thr Gly Thr Val Phe Ser
```

Figure 9B

| | | | | | | | | | |
|---|---|---|---|---|---|---|---|---|---|
|451|Trp|Thr|His|Arg|Ser|Ala|Thr|Leu|Thr|Asn|Thr|Ile|Asp|Pro|Glu|
|466|Arg|Ile|Asn|Gln|Ile|Pro|Leu|Val|Lys|Gly|Phe|Arg|Val|Trp|Gly|
|481|Gly|Thr|Ser|Val|Ile|Thr|Gly|Pro|Gly|Phe|Thr|Gly|Gly|Asp|Ile|
|496|Leu|Arg|Arg|Asn|Thr|Phe|Gly|Asp|Phe|Val|Ser|Leu|Gln|Val|Asn|
|511|Ile|Asn|Ser|Pro|Ile|Thr|Gln|Arg|Tyr|Arg|Leu|Arg|Phe|Arg|Tyr|
|526|Ala|Ser|Ser|Arg|Asp|Ala|Arg|Val|Ile|Val|Leu|Thr|Gly|Ala|Ala|
|541|Ser|Thr|Gly|Val|Gly|Gly|Gln|Val|Ser|Val|Asn|Met|Pro|Leu|Gln|
|556|Lys|Thr|Met|Glu|Ile|Gly|Glu|Asn|Leu|Thr|Ser|Arg|Thr|Phe|Arg|
|571|Tyr|Thr|Asp|Phe|Ser|Asn|Pro|Phe|Ser|Phe|Arg|Ala|Asn|Pro|Asp|
|586|Ile|Ile|Gly|Ile|Ser|Glu|Gln|Pro|Leu|Phe|Gly|Ala|Gly|Ser|Ile|
|601|Ser|Ser|Gly|Glu|Leu|Tyr|Ile|Asp|Lys|Ile|Glu|Ile|Ile|Leu|Ala|
|616|Asp|Ala|Thr|Phe|Glu|Ala|Glu|Ser|Asp|Leu|Glu|Arg|Ala|Gln|Lys|
|631|Ala|Val|Asn|Ala|Leu|Phe|Thr|Ser|Ser|Asn|Gln|Ile|Gly|Leu|Lys|
|646|Thr|Asp|Val|Thr|Asp|Tyr|His|Ile|Asp|Gln|Val|Ser|Asn|Leu|Val|
|661|Asp|Cys|Leu|Ser|Asp|Glu|Phe|Cys|Leu|Asp|Glu|Lys|Arg|Glu|Leu|

Figure 9C

```
676 Ser Glu Lys Val Lys His Ala Lys Arg Leu Ser Asp Glu Arg Asn
691 Leu Leu Gln Asp Pro Asn Phe Arg Ile Thr Ile Asn Arg Gln Pro Asp
706 Arg Gly Trp Arg Gly Ser Thr Asp Val Tyr Ile Gln Gly Gly Asp
721 Asp Val Phe Lys Glu Asn Tyr Val Thr Leu Pro Gly Thr Val Asp
736 Glu Cys Tyr Pro Thr Tyr Leu Tyr Gln Lys Ile Asp Glu Ser Lys
751 Leu Lys Ala Tyr Thr Arg Tyr Glu Leu Arg Gly Tyr Ile Glu Asp
766 Ser Gln Asp Leu Glu Ile Tyr Leu Ile Arg Tyr Asn Ala Lys His
781 Glu Ile Val Asn Val Pro Gly Thr Gly Ser Leu Trp Pro Leu Ser
796 Ala Gln Ser Pro Ile Gly Lys Cys Gly Glu Pro Asn Arg Cys Ala
811 Pro His Leu Glu Trp Asn Pro Asp Leu Asp Cys Ser Cys Arg Asp
826 Gly Glu Lys Cys Ala His His Ser His His Phe Thr Leu Asp Ile
841 Asp Val Gly Cys Thr Asp Leu Asn Glu Asp Leu Gly Val Trp Val
856 Ile Phe Lys Ile Lys Thr Gln Asp Gly His Ala Arg Leu Gly Asn
871 Leu Glu Phe Leu Glu Glu Lys Pro Leu Leu Gly Glu Ala Leu Ala
886 Arg Val Lys Arg Ala Glu Lys Lys Trp Arg Asp Lys Arg Glu Lys
```

Figure 9D

| | | | | | | | | | | | | | | |
|---|---|---|---|---|---|---|---|---|---|---|---|---|---|---|
| 901 | Leu | Gln | Leu | Glu | Thr | Asn | Ile | Val | Tyr | Lys | Glu | Ala | Lys | Glu | Ser |
| 916 | Val | Asp | Ala | Leu | Phe | Val | Asn | Ser | Gln | Tyr | Asp | Arg | Leu | Gln | Val |
| 931 | Asp | Thr | Asn | Ile | Ala | Met | Ile | His | Ala | Ala | Asp | Lys | Arg | Val | His |
| 946 | Arg | Ile | Arg | Glu | Ala | Tyr | Leu | Pro | Glu | Leu | Ser | Val | Ile | Pro | Gly |
| 961 | Val | Asn | Ala | Ala | Ile | Phe | Glu | Glu | Leu | Glu | Gly | Arg | Ile | Phe | Thr |
| 976 | Ala | Tyr | Ser | Leu | Tyr | Asp | Ala | Arg | Asn | Val | Ile | Lys | Asn | Gly | Asp |
| 991 | Phe | Asn | Asn | Gly | Leu | Leu | Cys | Trp | Asn | Val | Lys | Gly | His | Val | Asp |
| 1006 | Val | Glu | Gln | Asn | Asn | His | Arg | Ser | Val | Leu | Val | Ile | Pro | Glu |
| 1021 | Trp | Glu | Ala | Glu | Val | Ser | Gln | Glu | Val | Arg | Val | Cys | Pro | Gly | Arg |
| 1036 | Gly | Tyr | Ile | Leu | Arg | Val | Thr | Ala | Tyr | Lys | Glu | Gly | Tyr | Gly | Glu |
| 1051 | Gly | Cys | Val | Thr | Ile | His | Glu | Ile | Glu | Asp | Asn | Thr | Asp | Glu | Leu |
| 1066 | Lys | Phe | Ser | Asn | Cys | Val | Glu | Glu | Glu | Val | Tyr | Pro | Asn | Asn | Thr |
| 1081 | Val | Thr | Cys | Asn | Tyr | Thr | Gly | Thr | Gln | Glu | Ser | Tyr | Glu | Thr | Gly |
| 1096 | Thr | Tyr | Thr | Ser | Arg | Asn | Gln | Gly | Tyr | Asp | Glu | Ala | Tyr | Gly | Asn |
| 1111 | Asn | Pro | Ser | Val | Pro | Ala | Asp | Tyr | Ala | Ser | Val | Tyr | Glu | Glu | Lys |
| 1126 | Ser | Tyr | Thr | Asp | Arg | Arg | Arg | Glu | Asn | Pro | Cys | Glu | Ser | Asn | Arg |
| 1141 | Gly | Tyr | Gly | Asp | Tyr | Thr | Pro | Leu | Pro | Ala | Gly | Tyr | Val | Thr | Lys |
| 1156 | Asp | Leu | Glu | Tyr | Phe | Pro | Glu | Thr | Asp | Lys | Val | Trp | Ile | Glu | Ile |
| 1171 | Gly | Glu | Thr | Glu | Gly | Thr | Phe | Ile | Val | Asp | Ser | Val | Glu | Leu | Leu |
| 1186 | Leu | Met | Glu | Glu | | | | | | | | | | | |

Fragment 1-*

Figure 9E

```
         5                  10                 15                 20
Met Glu Asn Asn Gln Cys Ile Pro Tyr Asn Cys Ser Leu Ser Asn Pro Glu Glu
ATG GAG AAT AAT CAA TGC ATA CCT TAC AAT TGT AGT TTA AGT AAT CCT GAA GAA 25                 30                 35                 40
Val Leu Asp Gly Glu Arg Ile Ser Thr Gly Asn Ser Ser Ile Asp Ile Ser Leu Ser
GTA CTT TTG GAT GGA GAA CGG ATA TCA ACT GGT AAT TCA TCA ATT GAT ATT TCT CTG TCA 45                 50                 55                 60
Leu Val Gln Phe Leu Val Ser Asn Phe Val Pro Gly Gly Phe Leu Val Gly Leu Ile
CTT GTT CAG TTT CTG GTA TCT AAC TTT GTA CCA GGG GGA TTT TTA GTT GGA TTA ATA 65                 70                 75                 80
Asp Phe Val Trp Gly Ile Val Gly Pro Ser Gln Trp Asp Ala Phe Leu Val Gln Ile Glu
GAT TTT GTA TGG GGA ATA GTT GGC CCT TCT CAA TGG GAT GCA TTT CTA GTA CAA ATT GAA
```

Figure 10A

```
                                             85                      90                      95                     100
Gln   Leu   Ile   Asn   Glu   Arg   Ile   Ala   Glu   Phe   Ala   Arg   Asn   Ala   Ala   Ile   Ala   Asn   Leu   Glu
CAA   TTA   ATT   AAT   GAA   AGA   ATA   GCT   GAA   TTT   GCT   AGG   AAT   GCT   GCT   ATT   GCT   AAT   TTA   GAA 105                     110                     115                     120
Gly   Leu   Gly   Asn   Asn   Phe   Asn   Ile   Tyr   Val   Glu   Ala   Phe   Lys   Trp   Glu   Glu   Asp   Pro
GGA   TTA   GGA   AAC   AAT   TTC   AAT   ATA   TAT   GTG   GAA   GCA   TTT   AAA   TGG   GAA   GAA   GAT   CCT 125                     130                     135                     140
Asn   Asn   Pro   Ala   Thr   Arg   Thr   Arg   Val   Ile   Asp   Arg   Phe   Arg   Ile   Leu   Asp   Gly   Leu   Leu
AAT   AAT   CCA   GCA   ACC   AGG   ACC   AGA   GTA   ATT   GAT   CGC   TTT   CGT   ATA   CTT   GAT   GGG   CTA   CTT 145                     150                     155                     160
Glu   Arg   Asp   Ile   Pro   Ser   Phe   Arg   Ile   Ser   Gly   Phe   Glu   Val   Pro   Leu   Leu   Ser   Val   Tyr
GAA   AGG   GAC   ATT   CCT   TCG   TTT   CGA   ATT   TCT   GGA   TTT   GAA   GTA   CCC   CTT   TTA   TCC   GTT   TAT 165                     170                     175                     180
Ala   Gln   Ala   Ala   Asn   Leu   His   Leu   Ala   Ile   Leu   Arg   Asp   Ser   Val   Ile   Phe   Gly   Glu   Arg
GCT   CAA   GCG   GCC   AAT   CTG   CAT   CTA   GCT   ATA   TTA   AGA   GAT   TCT   GTA   ATT   TTT   GGA   GAA   AGA
```

Figure 10B

```
                      185             190             195             200
Trp Gly Leu Thr Ile Asn Val Asn Tyr Asn Glu Asn Arg Leu Ile Arg His Ile Asp
TGG GGA TTG ACA ATA AAT GTC AAT TAT AAC GAA AAT AGA CTA ATT AGG CAT ATT GAT 205             210             215             220
Glu Tyr Ala Asp His Cys Ala Asn Thr Tyr Asn Arg Gly Leu Asn Asn Leu Pro Lys Ser
GAA TAT GCT GAT CAC TGT GCA AAT ACG TAT AAT CGG GGA TTA AAT AAT TTA CCG AAA TCT 225             230             235             240
Thr Tyr Gln Asp Trp Ile Thr Tyr Asn Arg Leu Arg Arg Asp Leu Thr Leu Thr Val Leu
ACG TAT CAA GAT TGG ATA ACA TAT AAT CGG TTA AGA AGA GAC TTA ACA TTG ACT GTA TTA 245             250             255             260
Asp Ile Ala Ala Phe Phe Pro Asn Tyr Asp Asn Arg Arg Tyr Pro Ile Gln Pro Val Gly
GAT ATC GCC GCT TTC TTT CCA AAC TAT GAC AAT AGG AGA TAT CCA ATT CAG CCA GTT GGT 265             270             275             280
Gln Leu Thr Arg Glu Val Tyr Thr Asp Pro Leu Ile Asn Phe Asn Pro Gln Leu Gln Ser
CAA CTA ACA AGG GAA GTT TAT ACG GAC CCA TTA ATT AAT TTT AAT CCA CAG TTA CAG TCT
```

Figure 10C

```
                285              290              295              300
Val Ala Gln Leu Pro Thr Phe Asn Val Met Glu Ser Ser Ala Ile Arg Asn Pro His Leu
GTA GCT CAA TTA CCT ACT TTT AAC GTT ATG GAG AGC AGC GCA ATT AGA AAT CCT CAT TTA 305              310              315              320
Phe Asp Ile Leu Asn Asn Leu Thr Ile Phe Thr Asp Trp Phe Ser Val Gly Arg Asn Phe
TTT GAT ATA TTG AAT AAT CTT ACA ATC TTT ACG GAT TGG TTT AGT GTT GGA CGC AAT TTT 325              330              335              340
Tyr Trp Gly Gly His Arg Val Ile Ser Leu Ile Gly Gly Asn Ile Thr Ser Pro
TAT TGG GGA GGA CAT CGA GTA ATA TCT CTT ATA GGT GGT AAC ATA ACA TCT CCT 345              350              355              360
Ile Tyr Gly Arg Ala Asn Gln Glu Pro Pro Arg Ser Phe Asn Gly Pro Val
ATA TAT GGA AGA GCG AAC CAG GAG CCT CCA AGA TCC TTT AAT GGA CCG GTA 365              370              375              380
Phe Arg Thr Leu Ser Asn Pro Thr Leu Arg Leu Leu Gln Gln Pro Ala Pro Pro
TTT AGG ACT TTA TCA AAT CCT ACT TTA CGA TTA TTA CAG CAA CCT GCG CCA CCA
```

Figure 10D

```
            385                 390                 395                 400
Phe Asn Leu Arg Gly Val Glu Gly Val Glu Phe Ser Thr Pro Thr Asn Ser Phe Thr Tyr
TTT AAT TTA CGT GGT GTT GAA GGA GTA GAA TTT TCT ACA CCT ACA AAT AGC TTT ACG TAT 405                 410                 415                 420
Arg Gly Arg Gly Thr Val Asp Ser Leu Thr Glu Leu Pro Pro Glu Asp Asn Ser Val Pro
CGA GGA AGA GGT ACG GTT GAT TCT TTA ACT GAA TTA CCG CCT GAG GAT AAT AGT GTG CCA 425                 430                 435                 440
Pro Arg Glu Gly Tyr Ser His Arg Leu Cys His Ala Thr Phe Val Gln Arg Ser Gly Thr
CCT CGC GAA GGA TAT AGT CAT CGT TTA TGT CAT GCA ACT TTT CAA AGA TCT GGA ACA 445                 450                 455                 460
Pro Phe Leu Thr Gly Val Val Phe Ser Trp Thr His Arg Ser Ala Thr Leu Thr Asn
CCT TTT TTA ACA GGT GTA GTA TTT TCT TGG ACG CAT CGT AGT GCA ACT CTT ACA AAT 465                 470                 475                 480
Thr Ile Asp Pro Glu Arg Ile Asn Gln Ile Pro Leu Val Lys Gly Phe Arg Val Trp Gly
ACA ATT GAT CCA GAG AGA ATT AAT CAA ATA CCT TTA GTG AAA GGA TTT AGA GTT TGG GGG
```

Figure 10E

|     |     |     |     |     | 485 |     |     |     | 490 |     |     |     | 495 |     |     |     | 500 |
| --- | --- | --- | --- | --- | --- | --- | --- | --- | --- | --- | --- | --- | --- | --- | --- | --- | --- |
| Gly | Thr | Ser | Val | Ile | Thr | Gly | Pro | Gly | Phe | Thr | Gly | Gly | Asp | Ile | Leu | Arg | Arg | Asn | Thr |
| GGC | ACC | TCT | GTC | ATT | ACA | GGA | CCA | GGA | TTT | ACA | GGA | GGG | GAT | ATC | CTT | CGA | AGA | AAT | ACC |

|     |     |     |     | 505 |     |     |     | 510 |     |     |     | 515 |     |     |     | 520 |
| --- | --- | --- | --- | --- | --- | --- | --- | --- | --- | --- | --- | --- | --- | --- | --- | --- |
| Phe | Gly | Asp | Phe | Arg | Val | Ser | Leu | Gln | Val | Asn | Ile | Ser | Pro | Ile | Thr | Gln | Arg | Tyr | Arg |
| TTT | GGT | GAT | TTT | CGT | GTA | TCT | CTA | CAA | GTC | AAT | ATT | TCA | CCA | ATT | ACC | CAA | AGA | TAC | CGT |

|     |     |     |     | 525 |     |     |     | 530 |     |     |     | 535 |     |     |     | 540 |
| --- | --- | --- | --- | --- | --- | --- | --- | --- | --- | --- | --- | --- | --- | --- | --- | --- |
| Leu | Arg | Phe | Arg | Tyr | Ala | Ser | Ser | Arg | Asp | Ala | Arg | Val | Ile | Val | Leu | Thr | Gly | Ala | Ala |
| TTA | AGA | TTT | CGT | TAC | GCT | TCC | AGT | AGG | GAT | GCA | CGA | GTT | ATA | GTA | TTA | ACA | GGA | GCG | GCA |

|     |     |     |     | 545 |     |     |     | 550 |     |     |     | 555 |     |     |     | 560 |
| --- | --- | --- | --- | --- | --- | --- | --- | --- | --- | --- | --- | --- | --- | --- | --- | --- |
| Ser | Thr | Gly | Val | Gly | Gln | Val | Asn | Met | Pro | Leu | Gln | Lys | Thr | Met | Glu | Ile |
| TCC | ACA | GGA | GTG | GGA | GGC | CAA | GTT | AGT | AAT | ATG | CCT | CTT | CAG | AAA | ACT | ATG | GAA | ATA |

|     |     |     |     | 565 |     |     |     | 570 |     |     |     | 575 |     |     |     | 580 |
| --- | --- | --- | --- | --- | --- | --- | --- | --- | --- | --- | --- | --- | --- | --- | --- | --- |
| Gly | Glu | Asn | Leu | Thr | Ser | Arg | Thr | Phe | Tyr | Thr | Asp | Phe | Ser | Asn | Pro | Phe | Ser | Phe |
| GGG | GAG | AAC | TTA | ACA | TCT | AGA | ACA | TTT | TAT | ACC | GAT | TTT | AGT | AAT | CCT | TTT | TCA | TTT |

Figure 10F

|   |   | 585 |   |   |   | 590 |   |   |   | 595 |   |   |   | 600 |
|---|---|---|---|---|---|---|---|---|---|---|---|---|---|---|
| Arg | Ala | Asn | Pro | Asp | Ile | Ile | Gly | Ile | Ser | Glu | Gln | Pro | Leu | Gly | Ala | Gly | Ser | Ile |
| AGA | GCT | AAT | CCA | GAT | ATA | ATT | GGG | ATA | AGT | GAA | CAA | CCT | CTA | GGT | GCA | GGT | TCT | ATT |

|   |   | 605 |   |   |   | 610 |   |   |   | 615 |   |   |   | 620 |
|---|---|---|---|---|---|---|---|---|---|---|---|---|---|---|
| Ser | Gly | Glu | Leu | Tyr | Ile | Asp | Lys | Ile | Ile | Leu | Ala | Asp | Ala | Thr | Phe | Glu |
| AGT | AGC | GAA | CTT | TAT | ATA | GAT | AAA | ATT | GAA | CTA | GCA | GAT | GCA | ACA | TTT | GAA |

|   |   | 625 |   |   |   | 630 |   |   |   | 635 |   |   |   | 640 |
|---|---|---|---|---|---|---|---|---|---|---|---|---|---|---|
| Ala | Glu | Ser | Asp | Leu | Glu | Arg | Ala | Gln | Lys | Ala | Val | Asn | Ala | Leu | Phe | Thr | Ser | Ser | Asn |
| GCA | GAA | TCT | GAT | TTA | GAA | AGA | GCA | CAA | AAG | GCG | GTG | AAT | GCC | CTG | TTT | ACT | TCT | TCC | AAT |

|   |   | 645 |   |   |   | 650 |   |   |   | 655 |   |   |   | 660 |
|---|---|---|---|---|---|---|---|---|---|---|---|---|---|---|
| Gln | Ile | Gly | Leu | Lys | Thr | Asp | Val | Thr | Asp | Tyr | His | Ile | Asp | Gln | Val | Ser | Asn | Leu | Val |
| CAA | ATC | GGG | TTA | AAA | ACC | GAT | GTG | ACG | GAT | TAT | CAT | ATT | GAT | CAA | GTA | TCC | AAT | TTA | GTG |

|   |   | 665 |   |   |   | 670 |   |   |   | 675 |   |   |   | 680 |
|---|---|---|---|---|---|---|---|---|---|---|---|---|---|---|
| Asp | Cys | Leu | Ser | Asp | Glu | Phe | Cys | Leu | Asp | Glu | Lys | Arg | Glu | Leu | Ser | Glu | Lys | Val | Lys |
| GAT | TGT | TTA | TCA | GAT | GAA | TTT | TGT | CTG | GAT | GAA | AAG | CGA | GAA | TTG | TCC | GAG | AAA | GTC | AAA |

Figure 10G

| | | 685 | | | | | 690 | | | | | 695 | | | | | 700 |
|---|---|---|---|---|---|---|---|---|---|---|---|---|---|---|---|---|---|
| His | Ala | Lys | Arg | Ser | Asp | Glu | Arg | Asn | Leu | Leu | Gln | Asp | Pro | Asn | Phe | Arg | Gly | Ile |
| CAT | GCG | AAG | CGA | CTC | AGT | GAT | CGG | AAT | TTA | CTT | CAA | GAT | CCA | AAC | TTC | AGA | GGG | ATC |

| | | 705 | | | | | 710 | | | | | 715 | | | | | 720 |
|---|---|---|---|---|---|---|---|---|---|---|---|---|---|---|---|---|---|
| Asn | Arg | Gln | Pro | Asp | Arg | Gly | Trp | Arg | Gly | Ser | Thr | Asp | Ile | Thr | Ile | Gln | Gly | Asp |
| AAT | AGA | CAA | CCA | GAC | CGT | GGC | TGG | AGA | GGA | AGT | ACA | GAT | ATT | ACC | ATC | CAA | GGA | GAT |

| | | 725 | | | | | 730 | | | | | 735 | | | | | 740 |
|---|---|---|---|---|---|---|---|---|---|---|---|---|---|---|---|---|---|
| Asp | Val | Phe | Lys | Glu | Asn | Tyr | Val | Thr | Leu | Pro | Gly | Thr | Val | Asp | Glu | Cys | Tyr | Pro | Thr |
| GAC | GTA | TTC | AAA | GAG | AAT | TAC | GTC | ACA | CTA | CCG | GGT | ACC | GTT | GAT | GAG | TGC | TAT | CCA | ACG |

| | | 745 | | | | | 750 | | | | | 755 | | | | | 760 |
|---|---|---|---|---|---|---|---|---|---|---|---|---|---|---|---|---|---|
| Tyr | Leu | Tyr | Gln | Lys | Ile | Asp | Glu | Ser | Lys | Leu | Lys | Ala | Tyr | Thr | Arg | Tyr | Glu | Leu | Arg |
| TAT | TTA | TAT | CAG | AAA | ATA | GAT | GAG | TCG | AAA | TTA | AAA | GCT | TAT | ACC | CGT | TAT | GAA | TTA | AGA |

| | | 765 | | | | | 770 | | | | | 775 | | | | | 780 |
|---|---|---|---|---|---|---|---|---|---|---|---|---|---|---|---|---|---|
| Gly | Tyr | Ile | Glu | Asp | Ser | Gln | Asp | Leu | Glu | Ile | Tyr | Leu | Ile | Arg | Tyr | Asn | Ala | Lys | His |
| GGG | TAT | ATC | GAA | GAT | AGT | CAA | GAC | TTA | GAA | ATC | TAT | TTG | ATC | CGT | TAC | AAT | GCA | AAA | CAC |

Figure 10H

```
              785                790                795                800
Glu Ile Val Asn Val Pro Gly Thr Gly Ser Leu Trp Pro Ala Gln Ser Pro Ile
GAA ATA GTA AAT GTG CCA GGC ACG GGT TCC CTT TGG CCG GCC CAA AGT CCA ATC 805                810                815                820
Gly Lys Cys Gly Glu Pro Asn Arg Cys Ala Pro His Leu Glu Trp Asn Pro Asp Leu Asp
GGA AAG TGT GGA GAA CCG AAT CGA TGC GCG CCA CAC CTT GAA TGG AAT CCT GAT CTA GAT 825                830                835                840
Cys Ser Cys Arg Asp Gly Glu Lys Cys Ala His His Ser His Phe Thr Leu Asp Ile
TGT TCC TGC AGA GAC GGG GAA AAA TGT GCA CAT CAT TCC CAT TTC ACC TTG GAT ATT 845                850                855                860
Asp Val Gly Cys Thr Asp Leu Asn Glu Leu Asp Leu Gly Val Trp Val Ile Phe Lys Ile Lys
GAT GTT GGA TGT ACA GAC TTA AAT GAG CTA GAC TTA GGT GTA TGG GTG ATA TTC AAG ATT AAG 865                870                875                880
Thr Gln Asp Gly His Ala Arg Leu Gly Asn Leu Glu Phe Leu Glu Lys Pro Leu Leu
ACG CAA GAT GGC CAT GCA AGA CTA GGG AAT CTA GAG TTT CTC GAA AAA CCA TTA TTA
```

Figure 10I

```
885   Gly Glu Ala Leu Ala  Arg Val Lys Arg Ala  Glu Lys Lys Trp Arg  Asp Lys Arg Glu Lys
      GGG GAA GCA CTA GCT  CGT GTG AAA AGA GCG  GAG AAG AAA TGG AGA  GAC AAA CGA GAG AAA
                           890                  895                  900

905   Leu Gln Leu Glu Thr  Asn Ile Val Tyr Lys  Glu Ala Lys Ser Val  Asp Ala Leu Phe
      CTG CAG TTG GAA ACA  AAT ATT GTT TAT AAA  GAG GCA AAA TCT GTA  GAT GCT TTA TTT
                           910                  915                  920

925   Val Asn Ser Gln Leu  Tyr Asp Arg Leu Gln  Val Asp Thr Asn Ile  Ala Met Ile His Ala
      GTA AAC TCT CAA TAT  GAT AGA TTA CAA GTG  GAT ACG AAC ATC ATG  GCA ATG ATT CAT GCG
                           930                  935                  940

945   Asp Lys Arg Val His  Arg Ile Arg Glu Ile  Ala Tyr Leu Pro Glu  Leu Ser Val Ile Pro Gly
      GAT AAA CGC GTT CAT  AGA ATC CGG GAA ATC  GCG TAT CTG CCA GAG  TTG TCT GTG ATT CCA GGT
                           950                  955                  960

965   Val Asn Ala Ala Ile  Phe Glu Glu Leu Gly  Arg Ile Phe Thr Ala  Tyr Ser Leu Tyr
      GTC AAT GCG GCC ATT  TTC GAA GAA TTA GGA  CGT ATT TTT ACA GCG  TAT TCC TTA TAT
                           970                  975                  980
```

Figure 10J

```
       985                                          990                                         995                                        1000
Asp Ala Arg Asn Val Ile Lys Asn Gly Asp Phe Asn Asn Gly Leu Leu Cys Trp Asn Val
GAT GCG AGA AAT GTC ATT AAA AAT GGC GAT TTC AAT AAT GGC TTA TTA TGC TGG AAC GTG 1005                                         1010                                        1015                                       1020
Lys Gly His Val Asp Val Glu Gln Asn His Arg Ser Val Leu Val Ile Pro Glu
AAA GGT CAT GTA GAT GTA GAA CAA AAC CAC CGT TCG GTC CTT GTT ATC CCA GAA 1025                                         1030                                        1035                                       1040
Trp Glu Ala Glu Val Ser Gln Glu Val Arg Val Cys Pro Gly Tyr Gly Arg Gly Tyr Ile Leu Arg
TGG GAG GCA GAA GTG TCA CAA GAG GTT CGT GTC TGT CCA GGT TAT GGC CGT GGC TAT ATC CTT CGT 1045                                         1050                                        1055                                       1060
Val Thr Ala Tyr Lys Glu Gly Tyr Gly Cys Val Thr Ile His Glu Ile Glu Asp
GTC ACA GCA TAT AAA GAG GGA TAT GGC TGC GTA ACG ATC CAT GAG ATC GAA GAC 1065                                         1070                                        1075                                       1080
Asn Thr Asp Glu Leu Lys Phe Ser Asn Cys Val Glu Glu Tyr Pro Asn Asn Thr
AAT ACA GAC GAA CTG AAA TTC AGC AAC TGT GTA GAA GAG TAT CCA AAC AAC ACA
```

Figure 10K

```
                                      1085                          1090                          1095                          1100
Val Thr Cys Asn Asn Tyr Thr Gly Thr Gln Glu Glu Tyr Glu Gly Thr Tyr Thr Ser Arg
GTA ACG TGT AAT AAT TAT ACT GGG ACT CAA GAA GAA TAT GAG GGT ACG TAC ACT TCT CGT 1105                          1110                          1115                          1120
Asn Gln Gly Tyr Asp Glu Ala Tyr Gly Asn Asn Pro Ser Val Pro Ala Asp Tyr Ala Ser
AAT CAA GGA TAT GAC GAA GCC TAT GGT AAT AAC CCT TCC GTA CCA GCT GAT TAC GCT TCA 1125                          1130                          1135                          1140
Val Tyr Glu Glu Lys Ser Tyr Thr Asp Gly Arg Arg Glu Asn Pro Cys Glu Ser Asn Arg
GTC TAT GAA GAA AAA TCG TAT ACA GAT GGA CGA GAG AAT CCT TGT GAA TCT AAC AGA 1145                          1150                          1155                          1160
Gly Tyr Gly Asp Tyr Thr Pro Leu Pro Ala Gly Tyr Val Thr Lys Asp Leu Glu Tyr Phe
GGC TAT GGG GAT TAC ACA CCA CTA CCG GCT GGT TAT GTA ACA AAG GAT TTA GAG TAC TTC 1165                          1170                          1175                          1180
Pro Glu Thr Asp Lys Val Trp Ile Glu Ile Gly Glu Thr Gly Thr Phe Ile Val Asp
CCA GAG ACC GAT AAG GTA TGG ATT GAG ATC GGA GAA ACA GGA ACA TTC ATC GTG GAT

1185
Ser Val Glu Leu Leu Leu Met Glu Glu
AGC GTG GAA TTA CTC CTT ATG GAG GAA
```

Figure 10L

```
           10         20         30         40         50         60
  1 ATGGAGAATA ATATTCAAAA TCAATGCGTA CCTTACAATT GTTTAAATAA TCCTGAAGTA
 61 GAAATATTAA ATGAAGAAAG AAGTACTGGC AGATTACCGT TAGATATATC CTTATCGCTT
121 ACACGTTTCC TTTTGAGTGA ATTTGTTCCA GGTGTGGGAG TTGCGTTTGG ATTATTTGAT
181 TTAATATGGG GTTTTATAAC TCCTTCTGAT TGGAGCTTAT TTCTTTTACA GATTGAACAA
241 TTGATTGAGC AAAGAATAGA AACATTGGAA AGGAACCGGG CAATTACTAC ATTACGAGGG 310        320        330        340        350        360
301 TTAGCAGATA GCTATGAAAT TTATATTGAA GCACTAAGAG AGTGGGAAGC AAATCCTAAT
361 AATGCACAAT TAAGGGAAGA TGTGCGTATT CGATTGCTA  ATACAGACGA CGCTTTAATA
421 ACAGCAATAA ATAATTTAC  ACTTACAAGT TTTGAAATCC CTCTTTATC  GGTCTATGTT
481 CAAGCGGCGA ATTTACATTT ATCACTATTA AGAGACGCTG TATCGTTTGG GCAGGGTTGG
541 GACTGGGATA TAGCTACTGT TAATAATCAT TATAATAGAT TATTCATAGA 610        620        630        640        650        660
601 TATACGAAAC ATTGTTTGGA CACATACAAT CAAGGATTAG AAAACTTAAG AGGTACTAAT
661 ACTCGACAAT GGGCAAGATT CAATCAGTTT AGGAGAGATT TAACACTTAC TGTATTAGAT
721 ATCGTTGCTC TTTTCCGAA  CTACGATGTT AGAACATATC CAATTCAAAC GTCATCCCAA
781 TTAACAAGGG AAATTTATAC AAGTTCAGTA ATTGAGGATT CTCCAGTTTC TGCTAATATA
841 CCTAATGGTT TTAATAGGGC GGAATTTGGA GTTAGACCGC CCCATCTTAT GGACTTTATG
```

Figure 11A

```
            910        920        930        940        950        960
 901 AATTCTTTGT TTGTAACTGC AGAGACTGTT AGAAGTCAAA CTGTGTGGGG AGGACACTTA
 961 GTTAGTTCAC GAAATACGGC TGGTAACCGT ATAAATTTCC CTAGTTACGG GGTCTTCAAT
1021 CCTGGTGGCG CCATTTGGAT TGCAGATGAG GATCCACGTC CTTTTATCG GACATTATCA
1081 GATCCCTGTT TTGTCCGAGG AGGATTGGGG AATCCTCATT ATGTACTGGG GCTTAGGGGA
1141 GTAGCATTTC AACAAACTGG TACGAACCAC ACCCGAACAT TTAGAAATAG TGGGACCATA 1210       1220       1230       1240       1250       1260
1201 GATTCTCTAG ATGAAATCCC ACCTCAGGAT AATAGTGGGG CACCTTGGAA TGATTATAGT
1261 CATGTATTAA ATCATGTTAC ATTTGTACGA TGGCCAGGTG AGATTTCAGG AAGTGATTCA
1321 TGGAGAGCTC CAATGTTTC TTGGACGCAC CGTAGTGCAA CCCCTACAAA TACAATTGAT
1381 CCGGAGAGGA TTACTCAAAT ACCATTGGTA AAAGCACATA CACTTCAGTC AGGTACTACT
1441 GTTGTAAGAG GGCCCGGGTT TACGGGAGGA GATATTCTTC GACGAACAAG TGGAGGACCA 1510       1520       1530       1540       1550       1560
1501 TTTGCTTATA CTATTGTTAA TATAAATGGG CAATTACCCC AAAGGTATCG TGCAAGAATA
1561 CGCTATGCCT CTACTACAAA TCTAAGAATT TACGTAACGG TTGCAGGTGA ACGGATTTTT
1621 GCTGGTCAAT TTAACAAAAC AATGGATACC GGTGACCCAT TAACATTCCA ATCTTTTAGT
1681 TACGCAACTA TTTTACATTC CCAATGAGCC AGAGTAGTTT CACAGTAGGT
1741 GCTGATACTT TTAGTTCAGG GAATGAAGTT TATATAGACA GATTTGAATT GATTCCAGTT
```

Figure 11B

```
1801 ACTGCAACAT TTGAAGCAGA ATATGATTTA GAAAGAGCAC AAAAGGCGGT GAATGCGCTG
1861 TTTACTTCTA TAAACCAAAT AGGGATAAAA ACAGATGTGA CGGATTATCA TATTGATCAA
1921 GTATCCAATT TAGTGGATTG TTTATCAGAT GAATTTGTC TGGATGAAAA GCGAGAATTG
1981 TCCGAGAAAG TCAAACATGC GAAGCGACTC AGTGATGAGC GGAATTTACT TCAAGATCCA
2041 AACTTCAAAG GCATCAATAG GCAACTAGAC CGTGGTTGGA GAGGAAGTAC GGATATTACC

2101 ATCCAAAGAG GAGATGACGT ATTCAAAGAA AATTATGTCA CACTACCAGG TACCTTTGAT
2161 GAGTGCTATC CAACGTATTT ATATCAAAAA ATAGATGAGT CGAAATTAAA ACCCTATACT
2221 CGTTATCAAT TAAGAGGGTA TATCGAGGAT AGTCAAGACT TAGAAATCTA TTTGATCCGC
2281 TATAATGCAA AACACGAAAC AGTAAATGTG CTAGGTACGG GTTCTTTATG GCCGCTTTCA
2341 GTCCAAAGTC CAATCAGAAA GTGTGGAGAA CCGAATCGAT GCGCGCCACA CCTTGAATGG

2401 AATCCTGATC TAGATTGTTC CTGCAGAGAC GGGGAAAAAT GTGCACATCA TTCCGATCAT
2461 TTCTCCTTGG ACATTGATGT TGGATGTACA GACTTAAATG AGGACTTAGA TGTATGGGTG
2521 ATATTCAAGA TTAAGACGCA AGATGGCCAT GCAAGACTAG GAAATCTAGA GTTTCTCGAA
2581 GAGAAACCAT TAGTCGGGGA AGCACTAGCT CGTGTGAAAA GAGCAGAGAA AAAATGGAGA
2641 GATAAACGTG AAAAATTGGA ATTGGAAACA AATATTGTTT ATAAAGAGGC AAAAGAATCT
```

Figure 11C

```
      2710       2720       2730       2740       2750       2760
2701  GTAGATGCTT TATTTGTAAA CTCTCAATAT GATCAATTAC AAGCGGATAC GAATATTGCC
2761  ATGATTCATG CGGCAGATAA ACGTGTTCAT AGAATTCGGG AAGCGTATCT TCCAGAGTTA
2821  TCTGTGATTC CGGGTGTAAA TGTAGACATT TTCGAAGAAT TAAAAGGGCG TATTTTCACT
2881  GCATTCTTCC TATATGATGC GAGAAATGTC GTGATTTCAA GTGATTTCAA TAATGGCTTA
2941  TCATGCTGGA ACGTGAAAGG GCATGTAGAT GTAGAAGAAC AAAACAACCA CCGTTCGGTC 3010       3020       3030       3040       3050       3060
3001  CTTGTTGTTC CGGAATGGGA AGCAGAAGTG TCACAAGAAG TTCGTGTCTG TCCGGGTCGT
3061  GGCTATATCC TTCGTGTCAC AGCGTACAAG GAGGATATG GAGAAGGTTG CGTAACCATT
3121  CATGAGATCG AGAACAATAC AGAGAACTG AAGTTTAGCA ACTGCGTAGA AGAGGAAGTC
3181  TATCCAAACA ACACGGTAAC GTGTAATGAT TATACTGCAA ATCAAGAAGA ATACGGGGT
3241  GCGTACACTT CCCGTAATCG TGGATATGAC GAAACTTATG GAAGCAATTC TTCTGTACCA 3310       3320       3330       3340       3350       3360
3301  GCTGATTATG CGTCAGTCTA TGAAGAAAAA TCGTATACAG ATGGACGAAG AGACAATCCT
3361  TGTGAATCTA ACAGAGGATA TGGGGATTAC ACCACCACTAC CAGCTGGCTA TGTGACAAAA
3421  GAATTAGAGT ACTTCCCAGA AACCGATAAG GTATGGATTG AGATCGGAGA AACGGAAGGA
3481  ACATTCATCG TGGACAGCGT GGAATTACTC CTTATGGAGG AA*
```

Figure 11D

|     |     |     |     |     | 5   |     |     |     |     | 10  |     |     |     |     | 15  |
| --- | --- | --- | --- | --- | --- | --- | --- | --- | --- | --- | --- | --- | --- | --- | --- |
| 1   | Met | Glu | Asn | Asn | Ile | Gln | Asn | Cys | Val | Pro | Tyr | Asn | Cys | Leu |
| 16  | Asn | Asn | Pro | Glu | Val | Glu | Ile | Leu | Asn | Glu | Glu | Arg | Ser | Thr | Gly |
| 31  | Arg | Leu | Pro | Leu | Asp | Ile | Ser | Leu | Ser | Leu | Thr | Arg | Phe | Leu | Leu |
| 46  | Ser | Glu | Phe | Val | Pro | Gly | Val | Gly | Val | Ala | Phe | Gly | Leu | Phe | Asp |
| 61  | Leu | Ile | Trp | Gly | Phe | Ile | Thr | Pro | Ser | Asp | Trp | Ser | Leu | Phe | Leu |
| 76  | Leu | Gln | Ile | Glu | Gln | Leu | Ile | Glu | Gln | Arg | Ile | Glu | Thr | Leu | Glu |
| 91  | Arg | Asn | Arg | Ala | Ile | Thr | Thr | Leu | Arg | Gly | Leu | Ala | Asp | Ser | Tyr |
| 106 | Glu | Ile | Tyr | Ile | Glu | Ala | Leu | Arg | Glu | Trp | Glu | Ala | Asn | Pro | Asn |
| 121 | Asn | Ala | Gln | Leu | Arg | Glu | Asp | Val | Arg | Ile | Arg | Phe | Ala | Asn | Thr |
| 136 | Asp | Asp | Ala | Leu | Ile | Thr | Ala | Ile | Asn | Asn | Phe | Thr | Leu | Thr | Ser |
| 151 | Phe | Glu | Ile | Pro | Leu | Leu | Ser | Val | Tyr | Val | Gln | Ala | Ala | Asn | Leu |
| 166 | His | Leu | Ser | Leu | Leu | Arg | Asp | Ala | Val | Ser | Phe | Gly | Gln | Gly | Trp |
| 181 | Gly | Leu | Asp | Ile | Ala | Thr | Val | Asn | Asn | His | Tyr | Asn | Arg | Leu | Ile |
| 196 | Asn | Leu | Ile | His | Arg | Tyr | Thr | Lys | His | Cys | Leu | Asp | Thr | Tyr | Asn |
| 211 | Gln | Gly | Leu | Glu | Asn | Leu | Arg | Gly | Thr | Asn | Thr | Arg | Gln | Trp | Ala |

Figure 12A

```
226 Arg Phe Asn Gln Phe Arg Arg Asp Leu Thr Leu Thr Val Leu Asp
241 Ile Val Ala Leu Phe Pro Asn Tyr Val Arg Thr Val Tyr Pro Ile
256 Gln Thr Ser Ser Gln Leu Thr Arg Glu Ile Tyr Thr Ser Ser Val
271 Ile Glu Asp Ser Pro Val Ser Ala Asn Ile Pro Asn Gly Phe Asn
286 Arg Ala Glu Phe Gly Val Arg Pro Pro His Leu Met Asp Phe Met
301 Asn Ser Leu Phe Val Thr Ala Glu Thr Val Arg Ser Gln Thr Val
316 Trp Gly Gly His Leu Val Ser Arg Asn Thr Ala Gly Asn Arg
331 Ile Asn Phe Pro Ser Tyr Gly Val Phe Asn Pro Gly Gly Ala Ile
346 Trp Ile Ala Asp Glu Pro Arg Phe Tyr Arg Thr Leu Ser
361 Asp Pro Val Phe Arg Gly Gly Phe Gly Asn Pro His Tyr Val
376 Leu Gly Leu Arg Gly Val Ala Phe Gln Gln Thr Gly Thr Asn His
391 Thr Arg Phe Arg Asn Ser Gly Thr Ile Asp Ser Leu Asp Leu Asp Glu
406 Ile Pro Gln Asp Asn Ser Gly Ala Pro Trp Asn Asp Tyr Ser
421 His Val Leu Asn His Val Thr Phe Val Arg Trp Pro Gly Glu Ile
436 Ser Gly Ser Asp Ser Arg Ala Pro Met Pro Ser Trp Thr His His His
```

Figure 12B

```
451  Arg Ser Ala Thr Pro Thr Asn Thr Ile Asp Pro Glu Arg Ile Thr
466  Gln Ile Pro Leu Val Lys Ala His Thr Leu Gln Ser Gly Thr Thr
481  Val Val Arg Gly Pro Gly Phe Thr Gly Gly Asp Ile Leu Arg Arg
496  Thr Ser Gly Gly Pro Phe Ala Tyr Thr Tyr Ile Val Asn Ile Gly Asn Gly
511  Gln Leu Pro Arg Gln Arg Tyr Ala Arg Ile Arg Tyr Ala Ser Thr
526  Thr Asn Leu Arg Ile Tyr Val Thr Val Ala Gly Glu Arg Ile Phe
541  Ala Gly Gln Phe Asn Lys Thr Met Asp Thr Gly Asp Pro Leu Thr
556  Phe Gln Ser Phe Ser Tyr Ala Thr Ile Asn Thr Ala Phe Thr Phe
571  Pro Met Ser Gln Ser Ser Phe Thr Val Gly Ala Asp Thr Phe Ser
586  Ser Gly Asn Glu Val Tyr Ile Asp Arg Phe Glu Leu Ile Pro Val
601  Thr Ala Thr Phe Glu Ala Glu Tyr Asp Leu Glu Arg Ala Gln Lys
616  Ala Val Asn Ala Leu Phe Thr Ser Ile Asn Gln Ile Gly Ile Lys
631  Thr Asp Val Thr Asp Tyr His Ile Asp Gln Val Ser Asn Leu Val
646  Asp Cys Leu Ser Asp Glu Phe Cys Leu Asp Glu Lys Arg Glu Leu
661  Ser Glu Lys Val Lys His Ala Lys Arg Leu Ser Asp Glu Arg Asn
```

Figure 12C

| | | | | | | | | | | | | | | |
|---|---|---|---|---|---|---|---|---|---|---|---|---|---|---|
| 676 | Leu | Leu | Gln | Asp | Pro | Asn | Phe | Lys | Gly | Ile | Asn | Arg | Gln | Leu | Asp |
| 691 | Arg | Gly | Trp | Arg | Gly | Ser | Thr | Asp | Ile | Thr | Ile | Gln | Arg | Gly | Asp |
| 706 | Asp | Val | Phe | Lys | Glu | Asn | Tyr | Val | Thr | Leu | Pro | Gly | Thr | Phe | Asp |
| 721 | Glu | Cys | Tyr | Pro | Thr | Tyr | Leu | Tyr | Gln | Lys | Ile | Asp | Glu | Ser | Lys |
| 736 | Leu | Lys | Pro | Tyr | Thr | Arg | Tyr | Gln | Leu | Arg | Gly | Tyr | Ile | Glu | Asp |
| 751 | Ser | Gln | Asp | Leu | Glu | Ile | Tyr | Leu | Ile | Arg | Tyr | Asn | Ala | Lys | His |
| 766 | Glu | Thr | Val | Asn | Val | Leu | Gly | Thr | Gly | Ser | Leu | Trp | Pro | Leu | Ser |
| 781 | Val | Gln | Ser | Pro | Ile | Arg | Lys | Cys | Gly | Glu | Pro | Asn | Arg | Cys | Ala |
| 796 | Pro | His | Leu | Glu | Trp | Asn | Pro | Asp | Leu | Asp | Cys | Ser | Cys | Arg | Asp |
| 811 | Gly | Glu | Lys | Cys | Ala | His | Ser | His | Phe | Ser | His | Phe | Ser | Leu | Asp | Ile |
| 826 | Asp | Val | Gly | Cys | Thr | Asp | Leu | Asn | Glu | Asp | Leu | Asp | Val | Trp | Val |
| 841 | Ile | Phe | Lys | Ile | Lys | Thr | Gln | Asp | Gly | His | Ala | Arg | Leu | Gly | Asn |
| 856 | Leu | Glu | Phe | Leu | Glu | Glu | Lys | Pro | Leu | Val | Gly | Glu | Ala | Leu | Ala |
| 871 | Arg | Val | Lys | Arg | Ala | Glu | Lys | Lys | Trp | Arg | Asp | Lys | Arg | Glu | Lys |
| 886 | Leu | Glu | Leu | Glu | Thr | Asn | Ile | Val | Tyr | Lys | Glu | Ala | Lys | Glu | Ser |
| 901 | Val | Asp | Ala | Leu | Phe | Val | Asn | Ser | Gln | Tyr | Asp | Leu | Gln | Leu | Ala |
| 916 | Asp | Thr | Asn | Ile | Ala | Met | Ile | His | Ala | Ala | Asp | Lys | Arg | Val | His |

Figure 12D

| | | | | | | | | |
|---|---|---|---|---|---|---|---|---|
| 931 | Arg | Ile | Arg | Glu | Ala | Tyr | Leu | Pro | Glu | Leu | Ser | Val | Ile | Pro | Gly |
| 946 | Val | Asn | Asp | Ile | Phe | Asp | Glu | Leu | Lys | Gly | Arg | Ile | Phe | Thr |
| 961 | Ala | Phe | Leu | Tyr | Asp | Arg | Ala | Asn | Val | Lys | Asn | Gly | Asp |
| 976 | Phe | Asn | Gly | Leu | Ser | Cys | Trp | Asn | Val | Lys | Gly | His | Val | Asp |
| 991 | Val | Glu | Gln | Asn | Asn | His | Arg | Ser | Val | Leu | Val | Pro | Glu |
| 1006 | Trp | Glu | Ala | Glu | Val | Ser | Gln | Glu | Val | Arg | Val | Cys | Pro | Gly | Arg |
| 1021 | Gly | Tyr | Ile | Leu | Arg | Val | Thr | Ala | Tyr | Lys | Glu | Gly | Tyr | Gly | Glu |
| 1036 | Gly | Cys | Val | Thr | Ile | His | Glu | Ile | Glu | Asn | Thr | Asp | Glu | Leu |
| 1051 | Lys | Phe | Ser | Asn | Cys | Val | Glu | Glu | Val | Tyr | Pro | Asn | Asn | Thr |
| 1066 | Val | Thr | Asn | Asp | Tyr | Thr | Ala | Gln | Glu | Glu | Tyr | Gly | Gly |
| 1081 | Ala | Tyr | Thr | Ser | Arg | Asn | Arg | Gly | Tyr | Asp | Glu | Thr | Tyr | Gly | Ser |
| 1096 | Asn | Ser | Val | Pro | Ala | Tyr | Ala | Ser | Val | Tyr | Glu | Glu | Lys |
| 1111 | Ser | Tyr | Thr | Asp | Gly | Arg | Arg | Asp | Asn | Pro | Cys | Glu | Ser | Asn | Arg |
| 1126 | Gly | Tyr | Gly | Asp | Tyr | Thr | Pro | Leu | Pro | Ala | Gly | Tyr | Val | Thr | Lys |
| 1141 | Glu | Leu | Glu | Tyr | Phe | Pro | Glu | Thr | Asp | Lys | Val | Trp | Ile | Glu | Ile |
| 1156 | Gly | Glu | Thr | Glu | Gly | Thr | Phe | Ile | Val | Asp | Ser | Val | Glu | Leu | Leu |
| 1171 | Leu | Met | Glu | Glu |

Fragment 1 -*

Figure 12E

```
Met Glu Asn Asn Ile Gln Asn Cys Val Pro Tyr Asn Cys Leu Asn Asn Pro Glu Val
ATG GAG AAT AAT ATT CAA AAT TGC GTA CCT TAC AAT TGT TTA AAT AAT CCT GAA GTA
                    5                   10                  15                  20

Glu Ile Leu Asn Glu Glu Arg Ser Thr Gly Arg Leu Pro Leu Asp Ile Ser Leu Ser Leu
GAA ATA TTA AAT GAA GAA AGA AGT ACT GGC AGA TTA CCG TTA GAT ATA TCC TTA TCG
        25                  30                  35                  40

Thr Arg Phe Leu Leu Ser Glu Phe Val Pro Gly Val Gly Val Ala Phe Gly Leu Phe Asp
ACA CGT TTC CTT AGT GAA TTT GTT CCA GGT GTG GGA GTT GCG TTT GGA TTA TTT GAT
        45                  50                  55                  60

Leu Ile Trp Gly Phe Ile Thr Pro Ser Asp Trp Ser Leu Phe Leu Leu Gln Ile Glu Gln
TTA ATA TGG GGT TTT ATA ACT CCT TCT GAT TGG AGC TTA TTT CTT TTA CAG ATT GAA CAA
        65                  70                  75                  80

Leu Ile Glu Gln Arg Ile Glu Thr Leu Glu Arg Asn Arg Ala Ile Thr Thr Leu Arg Gly
TTG ATT GAG CAA AGA ATA GAA ACA TTG GAA AGG AAC CGG GCA ATT ACT ACA TTA CGA GGG
        85                  90                  95                  100
```

Figure 13A

```
                    105                 110                 115                 120
Leu Ala Asp Ser Tyr Glu Ile Tyr Ile Glu Ala Leu Arg Glu Trp Glu Ala Asn Pro Asn
TTA GCA GAT AGC TAT GAA ATT TAT ATT GAA GCA CTA AGA GAG TGG GAA GCA AAT CCT AAT 125                 130                 135                 140
Asn Ala Gln Leu Arg Glu Asp Val Arg Ile Arg Phe Ala Asn Thr Asp Asp Ala Leu Ile
AAT GCA CAA TTA AGG GAA GAT GTG CGT ATT CGA TTT GCT AAT ACA GAC GAC GCT TTA ATA 145                 150                 155                 160
Thr Ala Ile Asn Asn Phe Thr Leu Thr Ser Phe Glu Ile Pro Leu Leu Ser Val Tyr Val
ACA GCA ATA AAT TTT ACA CTT ACA AGT TTT GAA ATC CCT CTT TTA TCG GTC TAT GTT 165                 170                 175                 180
Gln Ala Ala Asn Leu His Leu Ser Leu Leu Arg Asp Ala Val Ser Phe Gly Gln Gly Trp
CAA GCG GCG AAT TTA CAT TTA TCA CTA AGA GAC GCT GTA TCG TTT GGG CAG GGT TGG 185                 190                 195                 200
Gly Leu Asp Ile Ala Thr Val Asn Asn His Tyr Asn Arg Leu Ile Asn Leu Ile His Arg
GGA CTG GAT ATA GCT ACT GTT AAT AAT CAT TAT AAT AGA TTA ATA AAT CTT ATT CAT AGA
```

Figure 13B

```
                    205                 210                 215                 220
Tyr Thr Lys His Cys Leu Asp Thr Tyr Asn Gln Gly Leu Glu Asn Leu Arg Gly Thr Asn
TAT ACG AAA CAT TGT TTG GAC ACA TAC AAT CAA GGA TTA GAA AAC TTA AGA GGT ACT AAT 225                 230                 235                 240
Thr Arg Gln Trp Ala Arg Phe Asn Gln Phe Arg Arg Asp Leu Thr Leu Thr Val Leu Asp
ACT CGA CAA TGG GCA AGA TTC AAT CAG TTT AGG AGA GAT TTA ACA CTT ACT GTA TTA GAT 245                 250                 255                 260
Ile Val Ala Leu Phe Pro Asn Tyr Asp Val Arg Thr Tyr Pro Ile Gln Thr Ser Ser Gln
ATC GTT GCT CTT CCG AAC TAC GAT GTT AGA ACA TAT CCA ATT CAA ACG TCA TCC CAA 265                 270                 275                 280
Leu Thr Arg Glu Ile Tyr Thr Ser Ser Val Ile Glu Asp Ser Pro Val Ser Ala Asn Ile
TTA ACA AGG GAA ATT TAT ACA AGT TCA ATT GAG GAT TCT CCA GTT TCT GCT AAT ATA 285                 290                 295                 300
Pro Asn Gly Phe Asn Arg Ala Glu Phe Gly Val Arg Pro Pro His Leu Met Asp Phe Met
CCT AAT GGT TTT AAT AGG GCG GAA TTT GGA GTT AGA CCG CCC CAT CTT ATG GAC TTT ATG
```

Figure 13C

```
                    305             310             315             320
Asn Ser Leu Phe Val Thr Ala Glu Thr Val Arg Ser Gln Thr Val Trp Gly Gly His Leu
AAT TCT TTG TTT GTA ACT GCA GAG ACT GTT AGA AGT CAA ACT GTG TGG GGA GGA CAC TTA 325             330             335             340
Val Ser Arg Asn Thr Ala Gly Asn Arg Ile Asn Phe Pro Ser Tyr Gly Val Phe Asn
GTT AGT CGA AAT ACG GCT GGT AAC CGT ATA AAT TTC CCT AGT TAC GGG GTC TTC AAT 345             350             355             360
Pro Gly Ala Ile Trp Ile Ala Asp Glu Asp Pro Arg Pro Phe Tyr Arg Thr Leu Ser
CCT GGT GCC ATT TGG ATT GCA GAT GAG GAT CCA CGT CCT TTT TAT CGG ACA TTA TCA 365             370             375             380
Asp Pro Val Phe Val Arg Gly Gly Phe Gly Asn Pro His Tyr Val Leu Gly Leu Arg Gly
GAT CCT GTT GTC CGA GGA GGA TTT GGG AAT CCT CAT TAT GTA CTG GGG CTT AGG GGA 385             390             395             400
Val Ala Phe Gln Thr Gly Thr Asn His Thr Arg Thr Phe Arg Asn Ser Gly Thr Ile
GTA GCA TTT CAA ACT GGT ACG AAC CAC ACC CGA ACA TTT AGA AAT AGT GGG ACC ATA
```

Figure 13D

```
                         405                     410                     415                     420
Asp Ser Leu Asp Glu Ile Pro Pro Gln Asp Asn Ser Gly Ala Pro Trp Asn Asp Tyr Ser
GAT TCT CTA GAT GAA ATC CCA CCT CAG GAT AAT AGT GGG GCA CCT TGG AAT GAT TAT AGT 425                     430                     435                     440
His Val Leu Asn His Val Thr Phe Val Arg Trp Pro Gly Glu Ile Ser Gly Ser Asp Ser
CAT GTA TTA AAT CAT GTT ACA TTT GTA CGA TGG CCA GGT GAG ATT TCA GGA AGT GAT TCA 445                     450                     455                     460
Trp Arg Ala Pro Met Phe Ser Trp Thr His Arg Ser Ala Thr Pro Thr Asn Thr Ile Asp
TGG AGA GCT CCA ATG TTT TCT TGG ACG CAC CGT AGT GCA ACC CCT ACA AAT ACA ATT GAT 465                     470                     475                     480
Pro Glu Arg Ile Thr Gln Ile Pro Leu Val Lys Ala His Thr Leu Gln Ser Gly Thr Thr
CCG GAG AGG ATT ACT CAA ATA CCA TTG GTA AAA GCA CAT ACA CTT CAG TCA GGT ACT ACT 485                     490                     495                     500
Val Val Arg Gly Pro Gly Phe Thr Gly Gly Asp Ile Leu Arg Arg Thr Ser Gly Gly Pro
GTT GTA AGA GGG CCC GGG TTT ACG GGA GAT ATT CTT CGA CGA ACA AGT GGA GGA CCA
```

Figure 13E

```
                                505             510             515             520
Phe Ala Tyr Thr Ile Val Asn Ile Asn Gly Gln Leu Pro Gln Arg Tyr Arg Ala Arg Ile
TTT GCT TAT ACT ATT GTT AAT ATA AAT GGG CAA TTA CCC CAA AGG TAT CGT GCA AGA ATA 525             530             535             540
Arg Tyr Ala Ser Thr Thr Asn Leu Arg Ile Tyr Val Thr Val Ala Gly Glu Arg Ile Phe
CGC TAT GCC TCT ACT ACA AAT CTA AGA ATT TAC GTA ACG GTT GCA GGT GAA CGG ATT TTT 545             550             555             560
Ala Gly Gln Phe Asn Lys Thr Met Asp Thr Gly Asp Pro Leu Thr Phe Gln Ser Phe Ser
GCT GGT CAA TTT AAC AAA ACA ATG GAT ACC GGT GAC CCA TTA ACA TTC CAA TCT TTT AGT 565             570             575             580
Tyr Ala Thr Ile Asn Thr Ala Phe Thr Phe Pro Met Ser Gln Ser Ser Phe Thr Val Gly
TAC GCA ACT ATT AAT ACA GCT TTT ACA TTC CCA ATG AGC CAG AGT AGT TTC ACA GTA GGT
```

Figure 13F

```
                                           585                   590                   595                   600
Ala Asp Thr Phe Ser Ser Gly Asn Glu Val Tyr Ile Asp Arg Phe Glu Leu Ile Pro Val
GCT GAT ACT TTT AGT TCA GGG AAT GAA GTT TAT ATA GAC AGA TTT GAA TTG ATT CCA GTT 605                   610                   615                   620
Thr Ala Thr Phe Glu Ala Glu Tyr Asp Leu Glu Arg Ala Gln Lys Ala Val Asn Ala Leu
ACT GCA ACA TTT GAA GCA GAA TAT GAT TTA GAA AGA GCA CAA AAG GCG GTG AAT GCG CTG 625                   630                   635                   640
Phe Thr Ser Ile Ile Asn Gln Ile Gly Lys Thr Asp Val Thr Asp Tyr His Ile Asp Gln
TTT ACT TCT ATA AAC CAA ATA GGG AAA ACA GAT GTG ACG GAT TAT CAT ATT GAT CAA 645                   650                   655                   660
Val Ser Asn Leu Val Asp Cys Leu Ser Asp Glu Phe Cys Leu Asp Glu Lys Arg Glu Leu
GTA TCC AAT TTA GTG GAT TGT TTA TCA GAT GAA TTT TGT CTG GAT GAA AAG CGA GAA TTG 665                   670                   675                   680
Ser Glu Lys Val Lys His Ala Lys Arg Leu Ser Asp Glu Arg Asn Leu Leu Gln Asp Pro
TCC GAG AAA GTC AAA CAT GCG AAG CGA CTC AGT GAT GAG CGG AAT TTA CTT CAA GAT CCA
```

Figure 13G

```
                        685                690                695                700
Asn Phe Lys Gly Ile Asn Arg Gln Leu Asp Arg Gly Trp Arg Gly Ser Thr Asp Ile Thr
AAC TTC AAA GGC ATC AAT AGG CAA CTA GAC CGT GGT TGG AGA GGA AGT ACG GAT ATT ACC 705                710                715                720
Ile Gln Arg Gly Asp Asp Val Phe Lys Glu Asn Tyr Val Thr Leu Pro Gly Thr Phe Asp
ATC CAA AGA GGA GAT GAT GTA TTC AAA GAA AAT TAT GTC ACA CTA CCA GGT ACC TTT GAT 725                730                735                740
Glu Cys Tyr Pro Thr Tyr Leu Tyr Gln Lys Ile Asp Glu Ser Lys Leu Lys Pro Tyr Thr
GAG TGC TAT CCA ACG TAT TTA TAT CAA ATA GAT GAG TCG AAA TTA AAA CCC TAT ACT 745                750                755                760
Arg Tyr Gln Leu Arg Gly Tyr Ile Glu Asp Ser Gln Asp Leu Glu Ile Tyr Leu Ile Arg
CGT TAT CAA TTA AGA GGG TAT ATC GAG GAT AGT CAA GAC TTA GAA ATC TAT TTG ATC CGC 765                770                775                780
Tyr Asn Ala Lys His Glu Thr Val Asn Val Leu Gly Thr Gly Ser Leu Trp Pro Leu Ser
TAT AAT GCA AAA CAC GAA ACA GTA AAT GTG CTA GGT ACG GGT TCT TTA TGG CCG CTT TCA
```

Figure 13H

```
              785                 790                 795                 800
Val Gln Ser Pro Ile Arg Lys Cys Gly Glu Pro Asn Arg Cys Ala Pro His Leu Glu Trp
GTC CAA AGT CCA ATC AGA AAG TGT GGA GAA CCG AAT CGA TGC GCG CCA CAC CTT GAA TGG

Asn Pro Asp Leu Asp Cys Ser Cys Arg Asp  805 Gly Glu Lys Cys Ala His  815 His Ser His His
AAT CCT GAT CTA GAT TGT TCC TGC AGA GAC GGG GAA AAA TGT GCA CAT CAT TCG CAT CAT 825                 830                 835                 840
Phe Ser Leu Asp Ile Asp Val Gly Cys Thr Asp Leu Asn Glu Asp Leu Asp Val Trp Val
TTC TCC TTG GAC ATT GAT GTT GGA TGT ACA GAC TTA AAT GAG GAC TTA GAT GTA TGG GTG 845                 850                 855                 860
Ile Phe Lys Ile Lys Thr Gln Asp Gly His Ala Arg Leu Gly Asn Leu Glu Phe Leu Glu
ATA TTC AAG ATT AAG ACG CAA GAT GGC CAT GCA AGA CTA GGA AAT CTA GAG TTT CTC GAA 865                 870                 875                 880
Glu Lys Pro Leu Val Gly Glu Ala Leu Ala Arg Val Lys Arg Ala Glu Lys Lys Trp Arg
GAG AAA CCA TTA GTC GGG GAA GCA CTA GCT CGT GTG AAA AGA GCA GAG AAA AAA TGG AGA
```

Figure 13I

```
Asp Lys Arg Glu Lys Leu Glu Thr Asn Ile Val Tyr Lys Glu Ala Lys Glu Ser
GAT AAA CGT GAA AAA TTG GAA ACA AAT ATT GTT AAA GAG GCA AAA GAA TCT
        885             890             895             900

Val Asp Ala Leu Phe Val Asn Ser Gln Tyr Asp Gln Leu Ala Asp Thr Asn Ile Ala
GTA GAT GCT TTA TTT GTA AAC TCT CAA TAT GAT CAA TTA GCG GAT ACG AAT ATT GCC
        905             910             915             920

Met Ile His Ala Asp Lys Arg Val His Arg Ile Arg Glu Ala Tyr Leu Pro Glu Leu
ATG ATT CAT GCG GAT AAA CGT GTT CAT AGA ATT CGG GAA GCG TAT CTT CCA GAG TTA
        925             930             935             940

Ser Val Ile Pro Gly Val Asn Val Asp Ile Phe Glu Glu Leu Lys Gly Arg Ile Phe Thr
TCT GTG ATT CCG GGT GTA AAT GAC ATT TTC GAA GAA TTA AAA GGG CGT ATT TTC ACT
        945             950             955             960

Ala Phe Leu Tyr Asp Ala Arg Asn Val Ile Lys Asn Gly Asp Phe Asn Asn Gly Leu
GCA TTC CTA TAT GAT GCG AGA AAT GTC ATT AAA AAC GGT GAT TTC AAT AAT GGC TTA
        965             970             975             980
```

Figure 13J

```
            985              990              995             1000
Ser Cys Trp Asn Val Lys Gly His Val Asp Val Glu Glu Gln Asn Asn His Arg Ser Val
TCA TGC TGG AAC GTG AAA GGG CAT GTA GAT GTA GAA GAA CAA AAC CAC CGT TCG GTC 1005             1010             1015             1020
Leu Val Val Pro Glu Trp Glu Ala Glu Val Ser Gln Glu Val Arg Val Cys Pro Gly Arg
CTT GTT GTT CCG GAA TGG GAA GCA GAA GTG TCA CAA GAA GTT CGT GTC TGT CCG GGT CGT 1025             1030             1035             1040
Gly Tyr Ile Leu Arg Val Thr Ala Tyr Lys Glu Gly Tyr Gly Glu Gly Cys Val Thr Ile
GGC TAT ATC CTT CGT GTC ACA GCG TAC AAG GAG GGA TAT GGA GAA GGT TGC GTA ACC ATT 1045             1050             1055             1060
His Glu Ile Glu Asn Thr Asn Asn Thr Asp Glu Leu Lys Phe Ser Asn Cys Val Glu Glu Val
CAT GAG ATC GAG AAC ACG AAT ACA GAC GAA CTG AAG TTT AGC AAC TGC GTA GAA GAG GTC 1065             1070             1075             1080
Tyr Pro Asn Asn Thr Val Thr Cys Asn Asp Tyr Thr Ala Asn Gln Glu Glu Tyr Gly Gly
TAT CCA AAC AAC ACG GTA ACG TGT AAT GAT TAT ACT GCA AAT CAA GAA GAA TAC GGG GGT
```

Figure 13K

```
                        1085                    1090                   1095                    1100
Ala Tyr Thr Ser Arg Asn Arg Gly Tyr Asp Glu Thr Tyr Gly Ser Asn Ser Ser Val Pro
GCG TAC ACT TCC CGT AAT CGT GGA TAT GAC GAA ACT TAT GGA AGC AAT TCT TCT GTA CCA 1105                    1110                   1115                    1120
Ala Asp Tyr Ala Ser Val Tyr Glu Glu Lys Ser Tyr Thr Asp Gly Arg Arg Asp Asn Pro
GCT GAT TAT GCG TCA GTC TAT GAA GAA AAA TCG TAT ACA GAT GGA CGA AGA GAC AAT CCT 1125                    1130                   1135                    1140
Cys Glu Ser Asn Arg Gly Tyr Gly Asp Tyr Thr Pro Leu Pro Ala Gly Tyr Val Thr Lys
TGT GAA TCT AAC AGA GGA TAT GGG GAT TAC ACA CCA CTA CCA GCT GGC TAT GTG ACA AAA 1145                    1150                   1155                    1160
Glu Leu Glu Tyr Phe Pro Glu Thr Asp Lys Val Trp Ile Glu Ile Gly Glu Thr Glu Gly
GAA CTA GAG TAC TTC CCA GAA ACC GAT AAG GTA TGG ATT GAG ATC GGA GAA ACG GAA GGA 1165                    1170
Thr Phe Ile Val Asp Ser Val Glu Leu Leu Leu Met Glu Glu
ACA TTC ATC GTG GAC AGC GTG GAA TTA CTC CTT ATG GAG GAA
```

Figure 13L

BACILLUS THURINGIENSIS ISOLATE ACTIVE AGAINST LEPIDOPTERAN PESTS, AND GENES ENCODING NOVEL LEPIDOPTERAN-ACTIVE TOXINS

CROSS-REFERENCE TO A RELATED APPLICATION

This is a continuation-in-part of copending application Ser. No. 371,955, filed Jun. 27, 1989.

BACKGROUND OF THE INVENTION

The most widely used microbial pesticides are derived from the bacterium *Bacillus thuringiensis*. This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. kurstaki HD-1 produces a crystal inclusion consisting of a biotoxin called a delta toxin which is toxic to the larvae of a number of lepidopteran insects. The cloning, sequencing, and expression of this B.t. crystal protein gene in *Escherichia coli* has been described in the published literature (Schnepf, H. E. and Whitely, H. R. [1981] Proc. Natl. Acad. Sci. USA 78: 2893-2897; Schnepf et al.). U.S. Pat. No. 4,448,885 and U.S. Pat. No. 4,467,036 both disclose the expression of B.t. crystal protein in *E. coli*.

BRIEF SUMMARY OF THE INVENTION

The subject invention concerns a novel *Bacillus thuringiensis* isolate designated B.t. PS81I which has activity against all lepidopteran pests tested.

Also disclosed and claimed are novel toxin genes which express toxins toxic to lepidopteran insects. These toxin genes can be transferred to suitable hosts via a plasmid vector.

Specifically, the invention comprises the novel B.t. isolate denoted B.t. PS81I, mutants thereof, and novel δ-endotoxin genes derived from this B.t. isolate which encode proteins which are active against lepidopteran pests.

BRIEF DESCRIPTION OF THE DRAWINGS

FIGS. 2A-2D. Nucleotide Sequence of toxin gene 81IA2.

FIGS. 3A-3E. Deduced amino acid sequence of toxin expressed by toxin gene 81IA2.

FIGS. 4A-4L. Composite of FIGS. 2 and 3.

FIG. 5A-5D. Nucleotide sequence of the toxin gene 81IB.

FIGS. 6A-6E. Deduced amino acid sequence of toxin expressed by toxin gene 81IB.

FIGS. 7A-7L. Composite of FIGS. 5 and 6.

FIGS. 8A-8D. Nucleotide sequence of the toxin gene 81IB2.

FIGS. 9A-9E. Deduced amino acid sequence of toxin expressed by toxin gene 81IB2.

FIG. 10A-10L. Composite of FIGS. 8 and 9.

FIGS. 11A-11D. Nucleotide sequence of the toxin gene 81IA.

FIGS. 12A-12E. Deduced amino acid sequence of toxin expressed by toxin gene 81IA.

FIGS. 13A-13L. Composite of FIGS. 11 and 12.

DETAILED DISCLOSURE OF THE INVENTION

Figure 1:
FIG. 1. Agarose gel electrophoresis of plasmid preparations from B.t. HD-1 (lane A) and B.t. PS81I (lane B).

The novel toxin genes of the subject invention were obtained from a novel lepidopteran-active *B. thuringiensis* (B.t.) isolate designated PS81I.

Characteristics of B.t. PS81I

Colony morphology—Large colony, dull surface, typical B.t.

Vegetative cell morphology—typical B.t.

Flagellar serotype—7, aizawai.

Intracellular inclusions—sporulating cells produce a bipyramidal crystal.

Plasmid preparations—agarose gel electrophoresis of plasmid preparations distinguishing B.t. PS81I from B.t. HD-1. See FIG. 1.

Alkali-soluble proteins—SDS-PAGE analysis shows a protein band at ca. 130,000 daltons.

Unique toxins—four unique toxins have been identified in B.t. PS81I.

Activity—B.t. PS81I kills all Lepidoptera tested.

Bioassay procedures:

B.t. PS81I spores and crystals were tested against: Beet Armyworm, *Spodoptera exigua*; Diamondback Moth, *Plutella xylostella*; Western Spruce Budworm, *Choristoneura occidentalis*.

LC50 values were as follows:

Beet Armyworm—2.53 ppm

Diamondback Moth—0.16 ppm

Western Spruce Budworm—3.2 ppm

Bioassay procedure: dilutions are prepared of a spore and crystal pellet, mixed with USDA Insect Diet (Technical Bulletin 1528, U.S. Department of Agriculture), and poured into small plastic trays. Larvae are placed on the diet mixture and held at 25° C. (late 2nd instar Diamondback Moth larvae, early 2nd instar Beet Armyworm larvae, 4th instar Western Spruce Budworm larvae). Mortality is recorded after six days.

*B. thuringiensis* PS81I, NRRL B-18484, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. B.t. PS81I, and mutants thereof, can be used to control lepidopteran pests.

A subculture of B.t. PS81I and the *E. coli* hosts harboring the toxin genes of the invention, were deposited in the permanent collection of the Northern Research Laboratory, U.S. Department of Agriculture, Peoria, Illinois, USA. The accession numbers and deposit dates are as follows:

| Subculture | Accession Number | Deposit Date |
| --- | --- | --- |
| B.t. PS81I | NRRL B-18484 | April 19, 1989 |
| *E. coli* (NM522) (pMYC392) | NRRL B-18498 | May 17, 1989 |
| *E. coli* (NM522) (pMYC393) | NRRL B-18499 | May 17, 1989 |
| *E. coli* (NM522) (pMYC394) | NRRL B-18500 | May 17, 1989 |

| Subculture | Accession Number | Deposit Date |
|---|---|---|
| *E. coli* (NM522) (pMYC1603) | NRRL B-18517 | June 30, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing a B.t. gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81I can be made by procedures well known in the art. For example, an asporogenous mutant can be obtained through ethylmethane sulfonate (EMS) mutagenesis of PS81I. The mutants can be made using ultraviolet light and nitrosoguanidine by procedures well known in the art.

A smaller percentage of the asporogenous mutants will remain intact and not lyse for extended fermentation periods; these strains are designated lysis minus ($-$). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. PS81I

A subculture of B.t. PS81I, or mutants thereof, can be used to inoculate the following medium, a peptone, glucose, salts medium.

| | |
|---|---|
| Bacto Peptone | 7.5 g/l |
| Glucose | 1.0 g/l |
| KH$_2$PO$_4$ | 3.4 g/l |
| K$_2$HPO$_4$ | 4.35 g/l |

-continued

| | |
|---|---|
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH | 7.2 |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Genes From Isolate PS81I and Transformation into *Escherichia coli*

Total cellular DNA was prepared from B.t. cells grown to a low optical density ($OD_{600}$=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81I and B.t.k. HD-1 was digested with EcoRI and separated by electrophoresis on a 0.8% (w/v) Agarose-TAE (50 mM Tris-Cl, 20 mM NaOAc, 2.5 mM EDTA, pH=8.0) buffered gel. A Southern blot of the gel was hybridized with a [$^{32}P$] radiolabeled probe against the 3.2 Kb NsiI to NsiI fragment of the toxin gene contained in plasmid pM3,130-7 of NRRL B-18332 and the 2.4 Kb NsiI to KpnI fragment of the "4.5 Kb class" toxin gene (Kronstad and Whitely [1986] Gene USA 43:29-40). These two fragments were combined and used as the probe. Results show that hybridizing fragments of PS81I are distinct from those of HD-1. Specifically, in the 1.5 Kb to 2.5 Kb size range, 2.3 Kb, 1.95 Kb, and 1.6 Kb hybridizing bands were detected in PS81I instead of the single 1.9 Kb hybridizing band in HD-1.

The following description outlines the steps taken in cloning two of the three EcoRI fragments described above. Two hundred micrograms of PS81I total cellular DNA was digested with EcoRI and separated by electrophoresis on a preparative 0.8% (w/v) Agarose-TAE gel. The 1.5 Kb to 2.3 Kb region of the gel was cut out and the DNA from it was electroeluted and concentrated using an ELUTIP TM -d (Schleicher and Schell, Keene, NH) ion exchange column according to the manufacturer's specification. The isolated EcoRI fragments were ligated to LAMBDA ZAP TM EcoRI arms (Stratagene Cloning Systems, La Jolla, Calif.) and packaged using Gigapak GOLD TM (Stratagene) extracts. The packaged recombinant phage were plated with *E. coli* strain BB4 (Stratagene) to give high plaque density. The plaques were screened by standard nucleic acid hybridization procedures with radiolabeled probe. The plaques that hybridized were purified and re-screened at a lower plaque density. The resulting purified phage were grown with R408 M13 helper phage (Stratagene) and the recombinant BlueScript TM (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by a standard rapid plasmid purification procedure to identify the desired plasmids. The plasmids, designated pM2,31-4 and pM2,31-1, contain approximately 1.95 Kb and 1.6 Kb EcoRI inserts, respectively. The DNA sequence of both inserts was determined using Stratagene's T7 and T3 oligonucleotide primers plus a set of existing internal B.t. endotoxin gene oligonucleotide primers. About 500 bp of the insert in pM2,31-4 was sequenced. In the same manner, approximately 1.0 Kb of the insert in pM2,31-1 was sequenced. Data analysis comparing the two sequences to other cloned and sequenced B.t. endotoxin genes showed that two distinct, unique partial toxin gene sequences had been found. Synthetic oligonucleotides were constructed to regions in both sequences that had minimum homology to other characterized B.t. endotoxin genes. The 42-mer oligonucleotide constructed to the sequence of the insert in pM2,31-4 was GGATACCGGTGACCCATTAACATTCCAATCTTTTAGTTACGC; it was used to isolate a toxin gene sequence called 81IA. The 40-mer oligonucleotide constructed to the sequence of the insert in pM2,31-1 was GAAGTTTATGGCCTCTTTCTGTAGAAAATCAAATTGGACC; it was used to isolate a toxin gene sequence called 81IB.

In order to clone both complete toxin genes, a Sau3A partial library was constructed. PS81I total cellular DNA partially digested with Sau3A and size fractionated by electrophoresis into a mixture of 9-23 Kb fragments on a 0.6% agarose-TAE gel, and purified as described previously, was ligated into LambdaGEM-11 TM (PROMEGA). The packaged phage were plated on P2392 *E. coli* cells (Stratagene) at a high titer and screened using the radiolabeled synthetic oligonucleotides (aforementioned) as nucleic acid hybridization probes. Hybridizing plaques, using each probe, were rescreened at a lower plaque density. Purified plaques that hybridized with either probe were used to infect P2392 *E. coli* cells in liquid culture for preparation of phage for DNA isolation. DNA was isolated by standard procedures. Preparative amounts of DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pUC19 (NEB). The ligation mix was introduced by transformation into DH5(α) competent *E. coli* cells (BRL) and plated on LB agar containing ampicillin, isopropyl-(β)-D-thiogalactoside (IPTG), and 5-bromo-4-chloro-3-indolyl-(β)-D-galactoside (XGAL). White colonies, with prospective insertions in the (β)-galactosidase gene of pUC19, were subjected to standard rapid plasmid purification procedures to isolate the desired plasmids. Plasmid pM3,122-1 contains a 15 Kb Sau3A fragment isolated using the 81IA oligonucleotide probe. Plasmid pM4,59-1 contains an 18 Kb Sau3A fragment isolated using the 81IB oligonucleotide probe.

Plasmid pM3,122-1 was digested with several restriction enzymes and Southern blotted. The blot was probed with the [$^{32}$P] radiolabeled 81IA specific oligonucleotide probe, as well as the labeled oligonucleotide sequencing primers made to known B.t.k. toxin genes. The resulting autoradiogram showed that two toxin genes were present in tandem on this cloned Sau3A fragment. Plasmid pM3,122-1 had a 4.0 Kb NdeI fragment that hybridized with oligonucleotide probes made to known B.t.k. genes. This fragment, however, did not hybridize with the specific oligonucleotides to 81IA or 81B; a new toxin gene had been discovered and subsequently was called 81IA2. The 4.0 Kb NdeI fragment was isolated and cloned in pUC19, yielding plasmid pMYC392. The 81IA toxin gene was isolated by digesting pM3,122-1 with HindIII, with resulting deletion of most of the 81IA2 toxin gene. The fragment was recircularized to form pMYC1603. The 81IA toxin gene is unique based on its restriction map and its DNA sequence.

Plasmid pM4,59-1 was digested with several restriction enzymes and Southern blotted. The blot was probed with the [$^{32}$P] radiolabeled 81IB specific oligonucleotide probe, as well as with labeled oligonucleotide sequencing primers made to known B.t.k. toxin genes. The plasmid pM4,59-1 was mapped and found to contain only a partial 81IB toxin gene. The full open reading frame (ORF) of a second toxin gene was discovered on the 18 Kb fragment and called 81IB2. The 81IB2 toxin gene was cloned separately from the 81IB toxin gene by digestion of pM4,59-1 with NdeI and SmaI, filling in the NdeI overhang and ligating the linear fragment back together. The resulting plasmid was called pMYC394. The full ORF of the 81IB toxin gene was isolated from another Sau3A fragment, cloned from the lambda library, on a 7.3 Kb HindIII fragment in pBluescript (Stratagene). The resulting plasmid is pMYC393.

The toxin genes were sequenced by the standard Sanger dideoxy chain termination method using oligonucleotide primers made to the "4.5 Kb class" toxin gene and by "walking" with primers made to the sequences of the new toxin genes. Sequence analysis of the four toxin genes has elucidated unique open reading frames and has deduced unique endotoxin proteins (Tables 1-12). The following table summarizes the size of each ORF in base pairs and the deduced endotoxin molecular weight in daltons.

| TOXIN GENE | ORF (bp) | DEDUCED MW (daltons) | Figure |
|---|---|---|---|
| 81IA2 | 3537 | 133,367 | 1-3 |
| 81IB | 3495 | 132,480 | 4-6 |
| 81IB2 | 3567 | 134,714 | 7-9 |
| 81IA | 3716 | 133,621 | 10-12 |

Endotoxin proteins have been expressed in Pseudomonas and/or Bacillus from the toxin genes. SDS-PAGE/Western blot analysis, using polyclonal antibodies directed against the "6.6 Kb" class toxin, verified that each gene encodes an immunoreactive protein of approximately 130,000 daltons. The toxin proteins encoded by the genes of the subject invention expressed in either a Bacillus or Pseudomonas host have activity against all lepidopteran insects tested: *Trichoplusia ni*, *Spodoptera exigua*, *Plutella xylostella*, and *Choristoneura occidentalis*.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual*, Cold Spring Harbor Laboratory, N.Y. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., New England Biolabs, Beverly, Mass., or Boehringer-Mannheim, Indianapolis, Ind. The enzymes are used according to the instructions provided by the supplier.

The plasmids containing the B.t. toxin genes can be removed from the transformed host microbes by use of standard well-known procedures. For example, the host microbes can be subjected to cleared lysate isopycnic density gradient procedures, and the like, to recover the desired plasmid.

EXAMPLE 3

Insertion of Toxin Genes Into Plants

The novel genes coding for the novel insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel *B. thuringiensis* Genes Into Baculoviruses

The novel genes of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399-406), and pAC380, described by Smith et al.

(Smith, G. E., Summers, M. D. and Fraser, M. J. [1983] Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequences encoding the novel B.t. toxin genes are shown in FIGS. 1, 4, 7, and 10. The deduced amino acid sequences are shown in FIGS. 2, 5, 8, and 11.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence with thymine substituted for uracil. The letters stand for the purine or pyrimidine bases forming the deoxynucleotide sequence:
A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the novel amino acid sequences of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is retained to some degree.

We claim:

1. An isolated DNA encoding a *Bacillus thuringiensis* toxin having an nucleotide sequence shown in FIG. 11.

2. DNA according to claim 1, encoding the amino acid sequence shown in FIG. 12.

3. A recombinant DNA transfer vector comprising DNA having a nucleotide sequence which codes for the amino acid sequence shown in FIG. 12.

4. The vector comprising DNA, according to claim 3, wherein said DNA has the sequence shown in FIG. 11.

5. A prokaryotic or eukaryotic host harboring the DNA transfer vector of claim 3.

6. A microorganism transformed to express a *Bacillus thuringiensis* toxin gene having the nucleotide sequence shown in FIG. 11.

7. The microorganism containing a toxin, according to claim 6, wherein said toxin has the sequence shown in FIG. 12.

8. A microorganism according to claim 6, which is a species of Pseudomonas, Azotobacter, Erwinia, Serratia, Klebsiella, Rhizobium, Rhodopseudomonas, Methylophilius, Agrobacterium, Acetobacter, Alcaligenes, Bacillus, or Streptomyces.

9. A microorganism according to claim 8, wherein said microorganism is pigmented and phylloplane adherent.

10. *Escherichia coli* transformed with a plasmid vector containing a *Bacillus thuringiensis* toxin gene having the nucleotide sequence shown in FIG. 11.

11. The *Escherichia coli* transformed to express a toxin, according to claim 10, wherein said toxin has the amino acid sequence shown in FIG. 12.

12. A transformed host *Escherichia coli* (NM522)(pMYC1603), having all the identifying characteristics of NRRL B-18517.

13. A plasmid pMYC1603.

* * * * *

UNITED STATES PATENT AND TRADEMARK OFFICE
CERTIFICATE OF CORRECTION

PATENT NO.     :   5,188,960

DATED          :   February 23, 1993

INVENTOR(S)    :   Jewel M. Payne and August J. Sick

It is certified that error appears in the above-identified patent and that said Letters Patent is hereby corrected as shown below:

Column 11, line 49:  Delete "(Tables 1-12)" and insert --(Figures 2-13)--.

Column 11, line 56:  Delete "1-3" and insert --2-4--.

Column 11, line 57:  Delete "4-6" and insert --5-7--.

Column 11, line 58:  Delete "7-9" and insert --8-10--.

Column 11, line 59:  Delete "10-12" and insert --11-13--.

Column 9, line 64:  Delete "Schell" and insert --Schuell--.

Column 12, line 48:  Delete "plant cells in bacteria" and insert --plant cells and in bacteria--.

Signed and Sealed this

Fifth Day of July, 1994

Attest:

BRUCE LEHMAN

*Attesting Officer*  *Commissioner of Patents and Trademarks*